US012502317B2

(12) United States Patent
Edwards et al.

(10) Patent No.: US 12,502,317 B2
(45) Date of Patent: Dec. 23, 2025

(54) LOW-PROFILE FLUID CONDUCTORS WITH MOISTURE MANAGEMENT FEATURES

(71) Applicant: Solventum Intellectual Properties Company, Maplewood, MN (US)

(72) Inventors: Thomas Alan Edwards, Hampshire (GB); Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 916 days.

(21) Appl. No.: 17/629,657

(22) PCT Filed: Jul. 22, 2020

(86) PCT No.: PCT/IB2020/056912
§ 371 (c)(1),
(2) Date: Jan. 24, 2022

(87) PCT Pub. No.: WO2021/019372
PCT Pub. Date: Feb. 4, 2021

(65) Prior Publication Data
US 2022/0218892 A1 Jul. 14, 2022

Related U.S. Application Data

(60) Provisional application No. 62/878,804, filed on Jul. 26, 2019.

(51) Int. Cl.
*A61F 13/05* (2024.01)
*A61M 1/00* (2006.01)

(52) U.S. Cl.
CPC ............. *A61F 13/05* (2024.01); *A61M 1/915* (2021.05); *A61M 1/964* (2021.05); *A61M 1/85* (2021.05); *A61M 1/92* (2021.05)

(58) Field of Classification Search
CPC .................... A61F 13/05; A61F 13/046; A61F 2013/00246; A61F 2013/00251;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion for Corresponding Application No. PCT/IB2020/056912, mailed Oct. 13, 2020.
(Continued)

*Primary Examiner* — Adam Marcetich
*Assistant Examiner* — Timothy L Flynn

(57) ABSTRACT

An apparatus for conducting fluid may comprise a first layer, a second layer, and a third layer sealed to form a first fluid pathway and a second fluid pathway in a stacked relationship. An aperture may be disposed at a first end of the second fluid pathway. Upon the application of a negative pressure, fluid may be drawn through the third aperture, into the second fluid pathway, and through the first fluid pathway. The apparatus may be fluidly coupled to a dressing at a tissue site. At least a portion of the third layer may be configured to allow moisture to evaporate from a periwound into the second fluid pathway. The fluid drawn through the third aperture may aid in removal of the evaporated moisture within the second fluid pathway, as well as moisture directly from the periwound, to reduce the risk of maceration to the periwound.

12 Claims, 29 Drawing Sheets

(58) Field of Classification Search
CPC .. A61F 2013/00255; A61F 2013/00259; A61F 2013/00263; A61M 1/90; A61M 1/92; A61M 1/912; A61M 1/913; A61M 1/915; A61M 1/85; A61M 1/964; A61M 2205/7536
See application file for complete search history.

(56) References Cited

U.S. PATENT DOCUMENTS 2,632,443 A 3/1953 Lesher
2,682,873 A 7/1954 Evans et al.
2,910,763 A 11/1959 Lauterbach
2,969,057 A 1/1961 Simmons
3,066,672 A 12/1962 Crosby, Jr. et al.
3,367,332 A 2/1968 Groves
3,520,300 A 7/1970 Flower, Jr.
3,568,675 A 3/1971 Harvey
3,648,692 A 3/1972 Wheeler
3,682,180 A 8/1972 McFarlane
3,826,254 A 7/1974 Mellor
4,080,970 A 3/1978 Miller
4,096,853 A 6/1978 Weigand
4,139,004 A 2/1979 Gonzalez, Jr.
4,165,748 A 8/1979 Johnson
4,184,510 A 1/1980 Murry et al.
4,233,969 A 11/1980 Lock et al.
4,245,630 A 1/1981 Lloyd et al.
4,256,109 A 3/1981 Nichols
4,261,363 A 4/1981 Russo
4,275,721 A 6/1981 Olson
4,284,079 A 8/1981 Adair
4,297,995 A 11/1981 Golub
4,333,468 A 6/1982 Geist
4,373,519 A 2/1983 Errede et al.
4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Austad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,135,116 A 10/2000 Vogel et al.
6,241,747 B1 6/2001 Ruff
6,287,316 B1 9/2001 Agarwal et al.
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
7,846,141 B2 12/2010 Weston
8,062,273 B2 11/2011 Weston
8,216,198 B2 7/2012 Heagle et al.
8,251,979 B2 8/2012 Malhi
8,257,327 B2 9/2012 Blott et al.
8,398,614 B2 3/2013 Blott et al.
8,449,509 B2 5/2013 Weston
8,529,548 B2 9/2013 Blott et al.
8,535,296 B2 9/2013 Blott et al.
8,551,060 B2 10/2013 Schuessler et al.
8,568,386 B2 10/2013 Malhi
8,679,081 B2 3/2014 Heagle et al.
8,834,451 B2 9/2014 Blott et al.
8,926,592 B2 1/2015 Blott et al.
9,017,302 B2 4/2015 Vitaris et al.
9,050,398 B2 6/2015 Armstrong et al.
9,198,801 B2 12/2015 Weston
9,211,365 B2 12/2015 Weston
9,289,542 B2 3/2016 Blott et al.
2002/0077661 A1 6/2002 Saadat
2002/0115951 A1 8/2002 Norstrem et al.
2002/0120185 A1 8/2002 Johnson
2002/0143286 A1 10/2002 Tumey
2009/0227969 A1* 9/2009 Jaeb .................... A61F 13/05 604/313
2010/0087767 A1 4/2010 McNeil
2011/0230849 A1 9/2011 Coulthard et al.
2014/0163491 A1 6/2014 Schuessler et al.
2015/0080788 A1 3/2015 Blott et al.
2016/0051736 A1* 2/2016 Henley ................ A61M 1/982 604/24
2017/0043070 A1* 2/2017 Locke .................... A61M 1/64
2017/0189236 A1* 7/2017 Locke ............... A61F 13/01029
2017/0224891 A1* 8/2017 Locke ................ A61F 13/0206
2018/0125722 A1* 5/2018 Hoggarth .......... A61F 13/01029
2019/0117861 A1 4/2019 Locke et al.

FOREIGN PATENT DOCUMENTS

AU 755496 B2 12/2002
CA 2005436 A1 6/1990
DE 26 40 413 A1 3/1978
DE 43 06 478 A1 9/1994
DE 29 504 378 U1 9/1995
EP 0100148 A1 2/1984
EP 0117632 A2 9/1984
EP 0161865 A2 11/1985
EP 0358302 A2 3/1990

(56) References Cited

FOREIGN PATENT DOCUMENTS

| | | | |
|---|---|---|---|
| EP | 1018967 | A1 | 7/2000 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 0007653 | A1 | 2/2000 |
| WO | 2019083607 | A1 | 5/2019 |
| WO | 2020102214 | A1 | 5/2020 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and p. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts,

(56) References Cited

OTHER PUBLICATIONS edited by B.M. Kostyuchenok et al. (Moscow, U.S.S.R. Oct. 28-29, 1986) pp. 91-92 (“Bagautdinov II”).
V.A. Solovev, Dissertation Abstract, Treatment and Prevention of Suture Failures after Gastric Resection (S.M. Kirov Gorky State Medical Institute, Gorky, U.S.S.R. 1988) (“Solovev Abstract”).
V.A.C.® Therapy Clinical Guidelines: A Reference Source for Clinicians; Jul. 2007.

* cited by examiner

LOW-PROFILE FLUID CONDUCTORS WITH MOISTURE MANAGEMENT FEATURES

CROSS-REFERENCE TO RELATED APPLICATIONS

This application claims the benefit of priority to U.S. Provisional Application No. 62/878,804, filed on Jul. 26, 2019, which is incorporated herein by reference in its entirety.

TECHNICAL FIELD

The invention set forth in the appended claims relates generally to tissue treatment systems and more particularly, but without limitation, to low-profile distribution components for providing negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage". "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a low-profile elongate fluid conductor may include a first end and a second end. The first end may be configured to be coupled to a negative-pressure source and the second end may be coupled with a dressing. The fluid conductor may include a first fluid pathway and a second fluid pathway, wherein each of the first fluid pathway and the second fluid pathway extend from the first end to the second end of the fluid conductor. The fluid conductor may further include an aperture proximate the first end of the fluid conductor. The aperture may be disposed on a side of the fluid conductor configured to face a patient of the fluid conductor. The aperture may provide a controlled flow into the second fluid pathway. The second fluid pathway may be fluidly coupled to the first fluid pathway proximate the second end of the fluid conductor. If negative pressure is applied to the first fluid pathway, the second fluid pathway and the aperture are configured to draw fluid from the ambient environment through the aperture, into the second fluid pathway, and toward the second end of the fluid conductor.

In some embodiments, at least a portion of the side of the fluid conductor configured to face the patient may comprise a material having a high moisture-vapor transmission rate that can permit evaporated moisture to pass into the second fluid conductor.

For example, an apparatus for conducting fluid may comprise a first layer, a second layer, and a third layer. The second layer may have a first aperture. The third layer may have a second aperture and a third aperture. The first layer, the second layer, and the third layer may be sealed to form a first fluid pathway and a second fluid pathway in a stacked relationship, with the second layer between the first fluid pathway and the second fluid pathway. The first aperture may fluidly couple the first fluid pathway and the second fluid pathway. The first aperture may be fluidly coupled to the second aperture. The third aperture may be disposed at a first end of the second fluid pathway. The apparatus may further comprise a first spacer layer configured to support the first fluid pathway, and a port fluidly coupled to the first fluid pathway.

In more specific examples, upon the application of a negative pressure, the second fluid pathway and the third aperture are configured to draw fluid through the third aperture, into the second fluid pathway, and toward the second aperture.

In another example, an apparatus for coupling a dressing to a negative-pressure source may comprise a first fluid conductor having a first end and a second end, and a second fluid conductor having a first end and a second end, wherein the first fluid conductor and the second fluid conductor are in a stacked relationship. A first aperture may be located at the second end of the first fluid conductor. The first aperture may fluidly couple the first fluid conductor and the second fluid conductor. A second aperture may be located at the second end of the second fluid conductor. The second aperture may be configured to fluidly couple the first fluid conductor and the second fluid conductor to the dressing. A third aperture may be located at the first end of the second fluid conductor. The third aperture may be configured to fluidly couple the second fluid conductor to the ambient environment. The apparatus may further comprise a first spacer layer configured to support the first fluid conductor, and a port configured to fluidly couple the first fluid conductor to the negative-pressure source.

In another example, an apparatus for coupling a dressing to a negative-pressure source may comprise a first layer, a second layer, and an intermediate layer sealed to form a first fluid conductor between the first layer and the intermediate layer and a second fluid conductor between the second layer and the intermediate layer. The apparatus may further comprise a first spacer layer configured to support the first fluid conductor. A first aperture may be disposed in the intermediate layer configured to fluidly couple the first fluid conductor to the second fluid conductor. A second aperture may be disposed in the second layer configured to fluidly couple the first fluid conductor to the dressing. A third aperture may be disposed in the second layer configured to fluidly couple the second fluid conductor to the ambient environment. The first fluid conductor may be fluidly coupled to the negative-pressure source.

In another example, an apparatus for managing fluid in a system for treating a tissue site may comprise a top layer, an intermediate layer, a base layer, an applicator, and a bridge. The top layer may include a film having a plurality of cells having closed ends extending from a surface of the top layer. The intermediate layer may include a film coupled to the top layer and covering the plurality of cells forming a first seal around the perimeter. The first seal may form a first fluid pathway between the top layer and the intermediate layer. The base layer may include a film coupled to the intermediate layer forming a second seal around the perimeter. The second seal may form a second fluid pathway between the intermediate layer and the base layer. The applicator may be at one end of the first and second fluid pathways. The applicator may have a first aperture formed in a first end of the intermediate layer, and a second aperture formed in a first end of the base layer. The first aperture may expose a portion of the plurality cells to define a recessed space in the first fluid pathway. The recessed space may be configured to be fluidly coupled to the tissue site. The first aperture may also fluidly couple the first fluid pathway to the second fluid pathway. The second aperture may be fluidly coupled with the first aperture. The bridge may extend from the applicator to the other end of the first and second fluid pathways. The bridge may have a port formed in the top layer and a third aperture formed in the base layer. The port may be configured to fluidly couple the first fluid pathway to a negative-pressure source. The third aperture may be configured to fluidly couple the second fluid pathway to an ambient environment. Upon the application of negative pressure, the second fluid pathway and the third aperture may be configured to draw fluid from the ambient environment through the third aperture, into the second fluid pathway, and toward the tissue site.

In yet another example, an apparatus for managing fluid in a system for treating a tissue site may comprise a top layer, an intermediate layer, a base layer, a first aperture, a second aperture, a third aperture, and a port. The top layer may include a film having a plurality of cells having closed ends extending from a bottom surface of the top layer. The intermediate layer may include a film coupled to the top layer and covering the plurality of cells forming a first fluid conductor between the top layer and the intermediate layer. The base layer may include a film coupled to the intermediate layer forming a second fluid conductor between the intermediate layer and the base layer. The first aperture may be formed in a first end of the intermediate layer, wherein the first aperture may expose a portion of the plurality cells to define a recessed space in the first fluid conductor. The recessed space may be configured to be fluidly coupled to the tissue site. The first fluid conductor may be fluidly coupled to the second fluid conductor through the first aperture. The second aperture may be formed in a first end of the base layer, wherein the second aperture may be fluidly coupled with the first aperture. The third aperture may be formed in a second end of the base layer, wherein the third aperture may be configured to fluidly couple the second fluid conductor to an ambient environment. The port may be formed in a second end of the top layer, wherein the port may be configured to fluidly couple the first fluid conductor to a negative-pressure source. If negative pressure is applied to the first fluid conductor, the second fluid conductor and the third aperture may be configured to draw fluid from the ambient environment through the third aperture, into the second fluid conductor, and toward the tissue site.

In yet another example, an apparatus for providing negative-pressure treatment may comprise a first layer, a second layer, a first spacer layer, and a second spacer layer. The first layer may comprise a first film. The second layer may comprise a second film having a first aperture and a second aperture. The first spacer layer may comprise a film having a plurality of standoffs, wherein the standoffs extend toward the second layer. The second spacer layer may comprise a film having a third aperture concentric with the second aperture and a plurality of standoffs, wherein at least some of the standoffs extend toward the first spacer layer. The first layer, the first spacer layer, the second spacer layer, and the second layer may be assembled in a stacked relationship to form a first fluid conductor between the first spacer layer and the second spacer layer, and a second fluid conductor between the second spacer layer and the second layer.

In more specific examples, if negative pressure is applied to the first fluid conductor, fluid can be drawn through the first aperture, into the second fluid conductor, and toward the second aperture.

In other more specific examples, the second film may have a high moisture-vapor transmission rate and may be configured to permit vapor pass through the second layer into the second fluid conductor.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
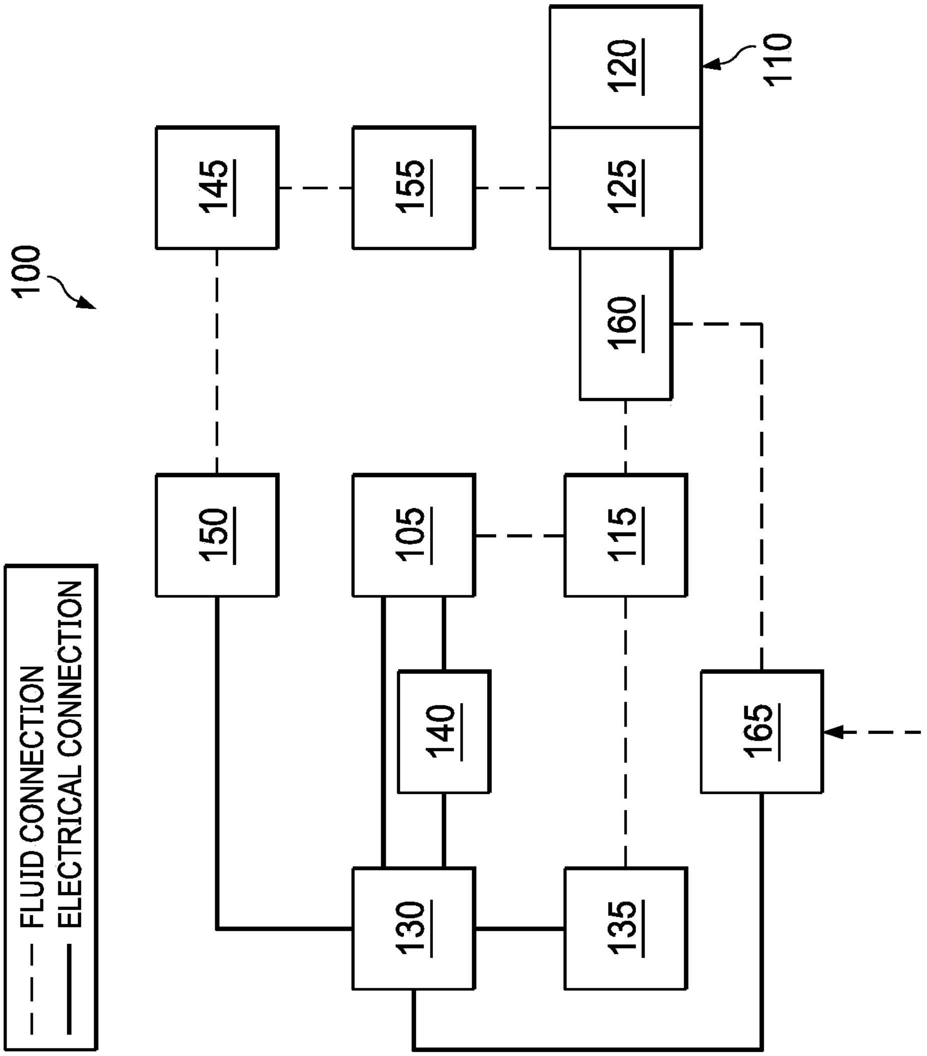
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. A tube, for example, is generally an elongated, flexible structure with a cylindrical lumen, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSAT.R.A.C.™ Pad, available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source, such as a positive-pressure source 150, a negative-pressure source, such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

In some examples, a bridge 160 may fluidly couple the dressing 110 to the negative-pressure source 105, as illustrated in FIG. 1. The therapy system 100 may also comprise a flow regulator, such as a regulator 165, fluidly coupled to a source of ambient air to provide a controlled or managed flow of ambient air. In some embodiments, the regulator 165 may be fluidly coupled to the tissue interface 120 through the bridge 160. In some embodiments, the regulator 165 may be positioned proximate to the container 115 and/or proximate a source of ambient air, where the regulator 165 is less likely to be blocked during usage.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols, such as polyester or polyether, isocyanate, such as toluene diisocyanate, and polymerization modifiers, such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment. In some embodiments, the regulator 165 may control the flow of ambient air to purge fluids and exudates from the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. In some examples, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative pressure from ambient pressure to the target pressure may not be instantaneous. For example, the negative-pressure source 105 and the dressing 110 may have an initial rise time, which can vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In other examples, a target pressure can vary with time in a dynamic pressure mode. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 2:
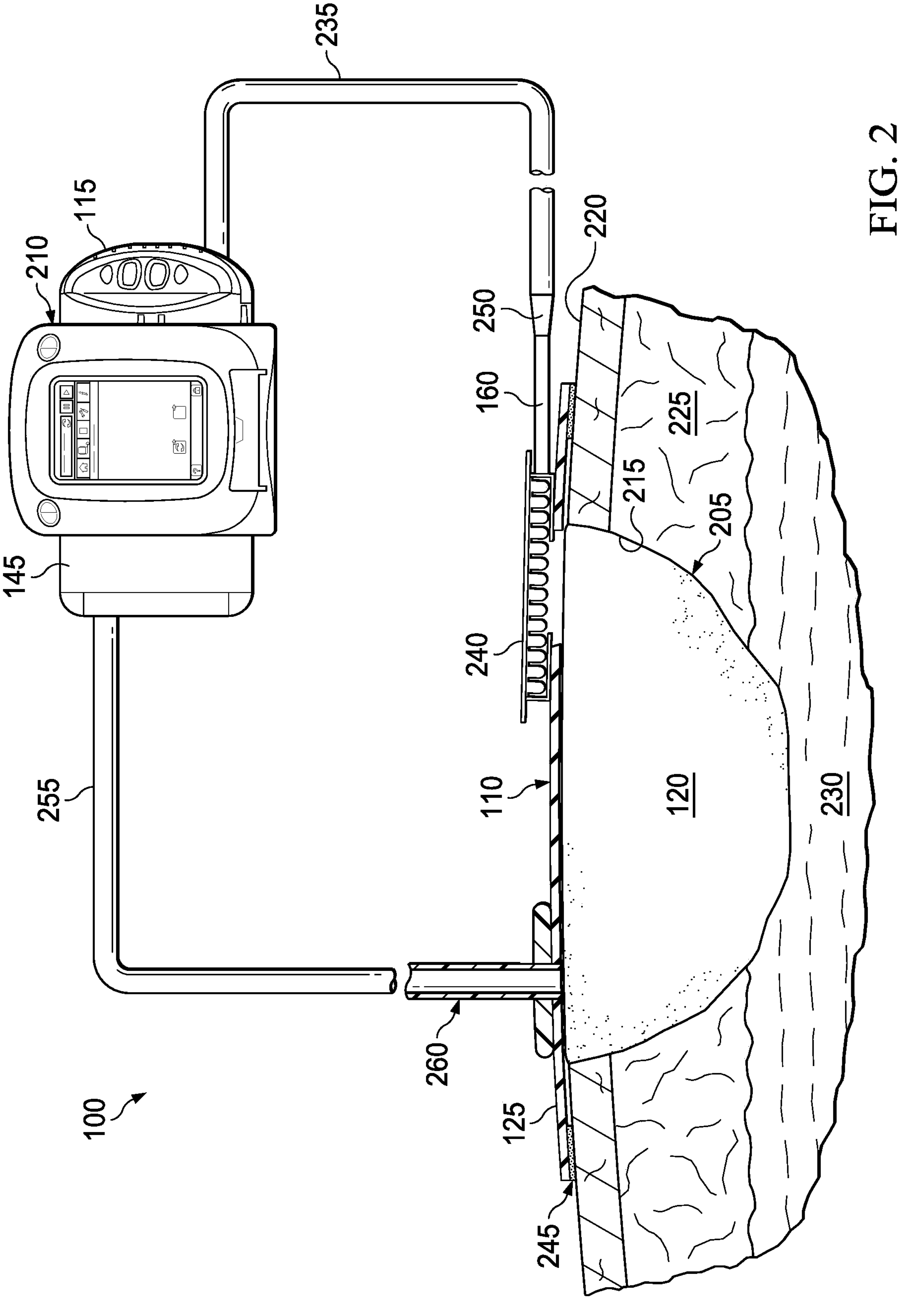
FIG. 2 is a schematic diagram of an example embodiment of the therapy system of FIG. 1 configured to apply negative pressure and treatment solutions to a tissue site.

FIG. 2 is a schematic diagram of an example embodiment of the therapy system 100 configured to apply negative pressure and treatment solutions to a tissue site 205. Some components of the therapy system 100 may be housed within or used in conjunction with other components, such as processing units, alarm indicators, memory, databases, software, display devices, or user interfaces that further facilitate therapy. For example, in some embodiments, the negative-pressure source 105 may be combined with the controller 130 and other components into a therapy unit, such as a therapy unit 210 illustrated in FIG. 2. The therapy unit 210 may be, for example, a V.A.C.ULTA™ Therapy Unit available from Kinetic Concepts, Inc. of San Antonio, Texas.

In the example of FIG. 2, the tissue site 205 is at least partially defined by a wound edge 215, which extends through an epidermal layer 220 and a dermal layer 225 and reaches into a hypodermis, or subcutaneous tissue 230. The therapy system 100 may be used to treat a wound of any depth, as well as many different types of wounds, including open wounds, incisions, or other tissue sites. Treatment of the tissue site 205 may include removal of fluids originating from the tissue site 205, such as exudates or ascites, or fluids instilled into the dressing to cleanse or treat the tissue site 205, such as antimicrobial solutions.

In the example of FIG. 2, a conduit 235 fluidly couples the container 115 to another fluid conductor, such as the bridge 160, which provides a fluid pathway between the conduit 235 and the tissue interface 120. The bridge 160 in the example of FIG. 2 is a substantially flat and flexible fluid conductor, but can also be compressed without occluding or blocking the fluid pathway between the conduit 235 and the tissue interface 120. In some embodiments, the bridge 160 may comprise or be coupled to an applicator 240 adapted to be positioned in fluid communication with the tissue interface 120 through an aperture in the cover 125. The cover 125 may be sealed to the epidermal layer 220 with an attachment device, such as an adhesive layer 245.

In some embodiments, the applicator 240 may be integral to the bridge 160. In other embodiments, the applicator 240 and the bridge 160 may be separate components that are coupled together to form a single device. In yet other embodiments, the applicator 240 and the bridge 160 may be separate components that may be used independently of each other in the therapy system 100.

The bridge 160 may have a substantially flat profile, and an adapter 250 may be configured to fluidly couple the bridge 160 to a tube or other round fluid conductor, such as the conduit 235 illustrated in the example of FIG. 2. In some embodiments, the adapter 250 may have one or more sealing valves, which can isolate the conduit 235 if separated from the bridge 160.

The example of FIG. 2 also illustrates a configuration of the therapy system 100 in which the solution source 145 is fluidly coupled to the tissue interface 120 through a conduit 255 and a dressing interface 260.

Figure 3A:
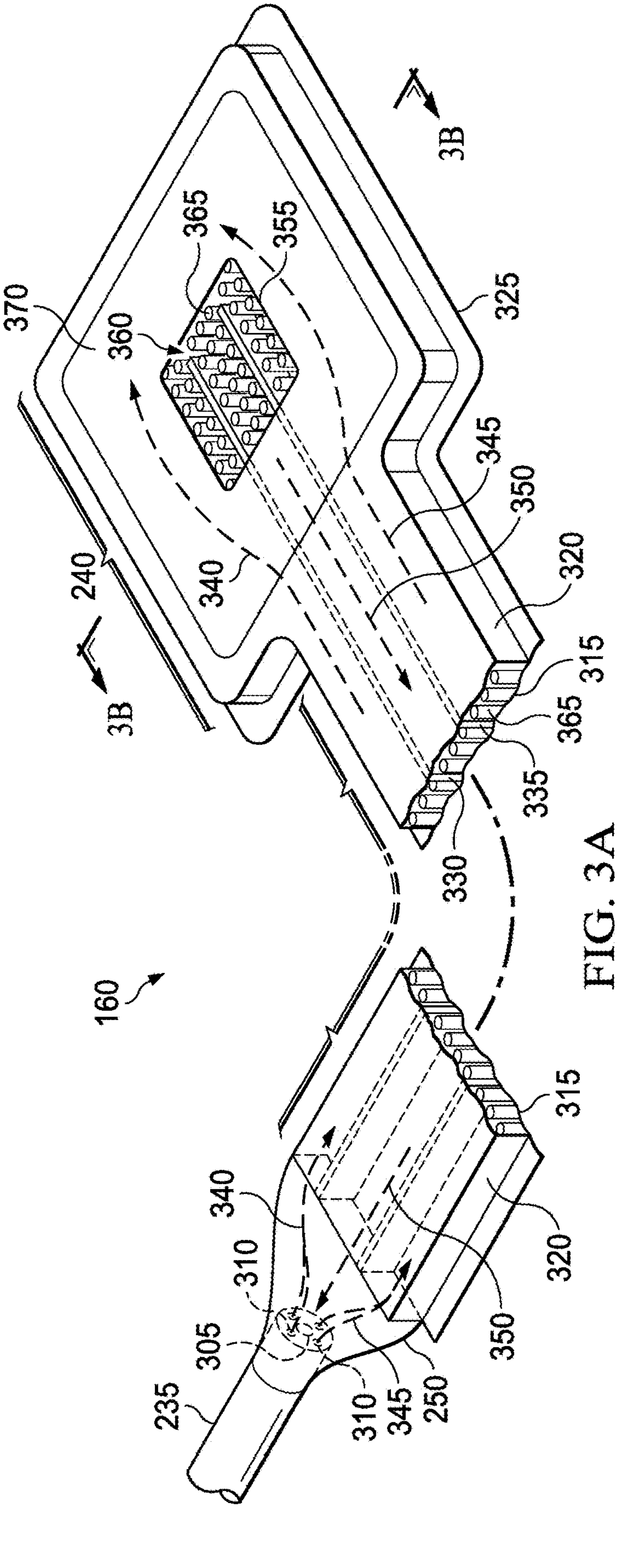
FIG. 3A is a segmented perspective bottom view of an example of a bridge that may be associated with some embodiments of the therapy system of FIG. 1.

FIG. 3A is a segmented perspective bottom view of an example of the bridge 160, illustrating additional details that may be associated with some embodiments. The bridge 160 of FIG. 3A generally has a low profile structure. FIG. 3A further illustrates features that may be associated with some embodiments of the applicator 240 of FIG. 2. The applicator 240 may be bulbous or any shape suitable for facilitating a connection to the dressing 110. The bridge 160 in the example of FIG. 3A is generally long and narrow. An adapter, such as the adapter 250, may fluidly couple the bridge 160 to a fluid conductor, such as the conduit 235. In some examples, the conduit 235 may be a multi-lumen tube in which a central lumen 305 is configured to couple the bridge 160 to a negative-pressure source, and one or more peripheral lumens 310 are configured to couple the bridge 160 to a sensor, such as the first sensor 135.

In some embodiments, the bridge 160 may comprise a liquid barrier formed from two layers. In FIG. 3A, for example, a periphery of a first layer 315 may be coupled to a second layer 320 to form a fluid path between two ends of the bridge 160, including the applicator 240. In some embodiments, one or both of the first layer 315 and the second layer 320 may be formed from or include a film of liquid-impermeable material. In some examples, the first layer 315, the second layer 320, or both may be formed from the same material as the cover 125. In some examples, the film forming the first layer 315, the second layer 320, or both may be a thin, flexible sheet. In some examples the film forming the first layer 315, the second layer 320, or both may be conformable. In some examples the film forming the first layer 315, the second layer 320, or both may have a low flexural modulus. In some examples the film forming the first layer 315, the second layer 320, or both may have an ultimate elongation of greater than 100%. In some examples, the film forming the first layer 315, the second layer 320, or both may be polymeric. In some examples, the film forming the first layer 315, the second layer 320, or both may be elastomeric. In some examples, the first layer 315, the second layer 320, or both may be transparent. In some examples, the first layer 315, the second layer 320, or both may be translucent. In some examples, the first layer 315, the second layer 320, or both may be opaque. The first layer 315 and the second layer 320 may be coupled around the periphery of the bridge 160 to form the sealed space by welding (RF or ultrasonic), heat sealing, or adhesive bonding, such as acrylics or cured adhesives. For example, the first layer 315 and the second layer 320 may be welded together around the periphery of the bridge 160 and may form a flange 325 around the periphery of the bridge 160 as a result of the weld.

The bridge 160 of FIG. 3A may further comprise at least one barrier or wall, such as a first wall 330, between the first layer 315 and the second layer 320. In some embodiments, the first wall 330 may extend from the end of the bridge 160 adjacent to the adapter 250 into the applicator 240 to form at least two sealed spaces or fluid pathways between the first layer 315 and the second layer 320 within the bridge 160. In some examples, the bridge 160 may further comprise a second barrier, such as a second wall 335, between the first layer 315 and the second layer 320. In some embodiments, the second wall 335 also may extend from the end of the bridge 160 adjacent to the adapter 250 into the applicator 240. In some example embodiments, the first wall 330 and the second wall 335 may comprise a polymeric film coupled to the first layer 315 and the second layer 320. In some other example embodiments, the first wall 330 and the second wall 335 may comprise a weld (RF or ultrasonic), a heat seal, an adhesive bond, or a combination of any of the foregoing. In some embodiments, the first wall 330 and the second wall 335 may form distinct fluid pathways within the sealed space between the first layer 315 and the second layer 320. In FIG. 3A, for example, the first wall 330 and the second wall 335 define in part a first pathway 340, a second pathway 345, and a third pathway 350. Each of the first pathway 340, the second pathway 345, and the third pathway 350 generally has a first end, a second end, and a longitudinal axis. In some embodiments, one or more of the fluid pathways may be fluidly coupled or configured to be fluidly coupled to the peripheral lumens 310, which can provide a pressure feedback path to a sensor, such as the first sensor 135. The third pathway 350 may be fluidly coupled to or configured to be fluidly coupled to the central lumen 305.

In some example embodiments, the first pathway 340, the second pathway 345, and the third pathway 350 may be fluidly coupled to the conduit 235 through the adapter 250. For example, the third pathway 350 may be fluidly coupled to the conduit 235 so that the third pathway 350 can deliver negative pressure to the tissue interface 120. Each of the first pathway 340 and the second pathway 345 may be fluidly coupled to a separate one of the peripheral lumens 310. In other embodiments, the first pathway 340 and the second pathway 345 both may be fluidly coupled to a common space within the adapter 250, which can be fluidly coupled to one or more of the peripheral lumens 310. In some example embodiments, the first pathway 340, the second pathway 345, and the third pathway 350 may terminate within the applicator 240. In some embodiments, the first pathway 340, the second pathway 345, and the third pathway 350 may be in fluid communication with each other within the applicator 240 for delivering and sensing negative pressure associated with the tissue interface 120.

The bridge 160 may comprise an opening or aperture, such as an aperture 355, adapted to fluidly couple the sealed space of the bridge 160 to the tissue interface 120. In FIG. 3A, for example, the aperture 355 is disposed in the applicator 240. A recessed space 360 within the bridge 160 can be adapted to be in fluid communication with the tissue interface 120 through the aperture 355 in use. In the example of FIG. 3A, the portions of first layer 315 and the second layer 320 at least partially define the recessed space 360 within the sealed space of the applicator 240. In some example embodiments, the first wall 330 and the second wall 335 may extend only partially into the recessed space 360 so that the ends of the first wall 330 and the second wall 335 are exposed by the aperture 355 as shown in the example of FIG. 3A. In some embodiments, the first pathway 340 and the second pathway 345 may be in fluid communication with the recessed space 360. The third pathway 350 may also be in fluid communication with the recessed space 360 and can be adapted to deliver negative pressure to the tissue interface 120 through the recessed space 360. In some example embodiments (not shown), the first wall 330 and the second wall 335 may extend beyond the aperture 355 so that less of the first pathway 340 and the second pathway 345 are exposed to negative pressure delivered to the tissue interface 120 to prevent or reduce occlusions and/or blockages.

The bridge 160 may further comprise a means for supporting fluid paths under pressure. In some embodiments, the means of support may comprise a plurality of support features, such as a flexible projections, standoffs, nodes, cells, porous textile, porous foam, or some combination of features disposed in a fluid path. For example, the bridge 160 of FIG. 3A comprises a plurality of supports 365. Adjacent to the aperture 355, the supports 365 may be adapted to come in direct contact with the tissue interface 120 in some examples. Support features such as the supports 365 can provide a cushion to prevent the sealed spaces of the bridge 160 from collapsing as a result of external forces. In some example embodiments, the supports 365 may come in contact with the second layer 320, and in some other example embodiments, the top portion of the supports 365 may be coupled to the second layer 320. In some example embodiments, the supports 365 may be disposed only in the applicator 240, and other support features may be disposed in the bridge 160 between the applicator 240 and the conduit 235.

The bridge 160 of FIG. 3A may also comprise an affixation surface 370 surrounding the aperture 355, which can be coupled to the dressing 110 or directly to a tissue site in some examples. In some embodiments, a top drape (not shown) may be utilized to cover the applicator 240 for additional protection and support over the applicator 240 if applied to a tissue site. In some embodiments, a top drape may also be utilized to cover any adhesive that might be exposed. In some embodiments, a top drape may be similar to the cover 125. For example, a top drape may comprise or consist essentially of a polymer, such as a polyurethane film.

Figure 3B:
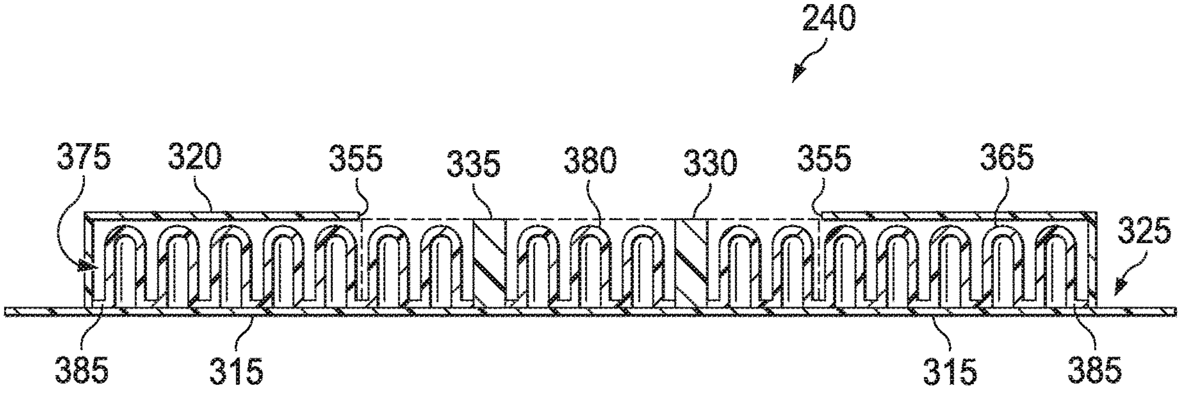
FIG. 3B is a schematic view of an applicator that may be associated with some embodiments of the bridge of FIG. 3A.

FIG. 3B is a schematic view of the applicator 240 of FIG. 3A, taken along line 3B-3B, illustrating additional details that may be associated with some embodiments. For example, some embodiments of the support features may be formed by sealing a spacer layer 375 to the first layer 315. In the example of FIG. 3B, each of the supports 365 comprises a standoff 380 in the spacer layer 375. In some embodiments, the standoffs 380 may be formed by blisters, bubbles, cells or other raised formations that extend above or below a base 385 of the spacer layer 375, for example. In some examples, the standoffs 380 may be vacuum-formed regions of the spacer layer 375.

The base 385 may be sealed to the first layer 315, and the standoffs 380 may extend from the first layer 315 toward the aperture 355 of the second layer 320 as illustrated in FIG. 3B. At least some of the supports 365 may be configured to come in direct contact with the tissue interface 120 through the aperture 355.

In some embodiments, the base 385 may be sealed to the first layer 315 so that the first layer 315 closes the standoffs 380. For example, the base 385 may be heat-sealed to the first layer 315 while the standoffs 380 may be vacuum-formed simultaneously. In other examples, the seal may be formed by adhesion between the first layer 315 and the spacer layer 375. Alternatively, the first layer 315 and the spacer layer 375 may be adhesively bonded to each other.

In general, the supports 365 are structured so that they do not completely collapse from apposition forces resulting from the application of negative pressure and/or external forces to the bridge 160. In some examples, the first layer 315 and the spacer layer 375 may be formed from separate sheets or film brought into superposition and sealed, or they may be formed by folding a single sheet onto itself with a heat-sealable surface facing inward. Any one or more of the first layer 315, second layer 320, and the spacer layer 375 also may be a monolayer or multilayer structure, depending on the application or the desired structure of the support features.

In some example embodiments, the standoffs 380 may be substantially airtight to inhibit collapsing of the standoffs 380 under negative pressure, which could block the flow of fluid through the bridge 160. For example, in the embodiment of FIG. 3B, the standoffs 380 may be substantially airtight and have an internal pressure that is an ambient pressure. In another example embodiment, the standoffs 380 may be inflated with air or other suitable gases, such as carbon dioxide or nitrogen. The standoffs 380 may be inflated to have an internal pressure greater than the atmospheric pressure to maintain their shape and resistance to collapsing under pressure and external forces. For example, the standoffs 380 may be inflated to a pressure up to about 25 psi above the atmospheric pressure.

In some embodiments, the first layer 315, the second layer 320, and the spacer layer 375 may each have a thickness within a range of 400 to 600 microns. For example, the first layer 315, the second layer 320, and the spacer layer 375 may be formed from thermoplastic polyurethane film having a thickness of about 500 microns. In some example embodiments, each may have a thickness of about 200 μm to about 600 μm. In some embodiments, a thickness of about 500 μm or about 250 μm may be suitable.

In some embodiments, one or more of the first layer 315, the second layer 320, and the spacer layer 375 may have a different thickness. For example, the thickness of the second layer 320 may be up to 50% thinner than the thickness of the spacer layer 375. If the fabrication process comprises injection molding, portions of the spacer layer 375 defining the standoffs 380 may have a thickness between about 400 μm and about 500 μm. However, if the standoffs 380 are fabricated by drawing a film, the spacer layer 375 proximate a top portion of the standoffs 380 may have a thickness as thin as 50 μm.

After the standoffs 380 have been fabricated, the walls of the standoffs 380 may have a thickness relative to the thickness of base 385. The relative thickness may be defined by a draw ratio, such as the ratio of the average height of the standoffs 380 to the average thickness of the spacer layer 375. In some example embodiments, the standoffs 380 may have a generally tubular shape, which may have been formed from the spacer layer 375 having various thicknesses and draw ratios. In some example embodiments, the spacer layer 375 may have an average thickness of 500 μm and the standoffs 380 may have an average height in a range between about 2.0 mm and 5.0 mm. Consequently, the standoffs 380 may have a draw ratio ranging from about 4:1 to about 10:1 for heights of 2.0 and 5.0 mm, respectively. In another example embodiment, the draw ratio may range from about 5:1 to about 13:1 where the thickness of the spacer layer 375 is an average of about 400 μm. In yet other example embodiments, the draw ratio may range from about 3:1 to about 9:1 where the thickness of the spacer layer 375 is an average of about 600 μm. In some embodiments, the standoffs 380 may have an average height in a range between about 1.0 mm and 4.0 mm, depending on the thickness of the spacer layer 375. The spacer layer 375 may have varying thicknesses and flexibilities, but is substantially non-stretchable so that the standoffs 380 maintain a generally constant volume if sealed to the first layer 315. Additionally, the standoffs 380 can support a load without bursting and can recover their original shape after a load is removed.

In some example embodiments, any one or more of the first layer 315, the second layer 320, and the spacer layer 375 may be formed from a non-porous, polymeric film that may comprise any flexible material that can be manipulated to form suitable support features, including various thermoplastic materials, e.g., polyethylene homopolymer or copolymer, polypropylene homopolymer or copolymer, etc. Non-limiting examples of suitable thermoplastic polymers may include polyethylene homopolymers, such as low density polyethylene (LDPE) and high density polyethylene (HDPE), and polyethylene copolymers such as, e.g., ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches, including linear low density polyethylene (LLDPE), linear medium density polyethylene (LMDPE), very low density polyethylene (VLDPE), and ultra-low density polyethylene (ULDPE). Various other materials may also be suitable, such as polypropylene homopolymer or polypropylene copolymer (e.g., propylene/ethylene copolymer), polyesters, polystyrenes, polyamides, polycarbonates, etc. In some example embodiments, one or more of the first layer 315, the second layer 320, and the spacer layer 375 may be formed from a polyether polyurethane film having a thickness in a range from about 68 microns to about 85 microns available under the part number 58240 from Avery Dennison Medical of Mentor, Ohio. In some embodiments, this polyether polyurethane film may have a thickness of about 80 microns. In some example embodiments, one or more of the first layer 315, the second layer 320, and the spacer layer 375 may be formed from a polyether polyurethane film having a thickness in a range from about 2.7 mil (about 68.58 microns) to about 3.3 mil (83.82 microns) available under the product number Argomed 18410D from Schweitzer-Mauduit International, Inc. of Alpharetta, Georgia. In some embodiments, the polyether polyurethane film may have a thickness of about 3 mil (about 76.2 microns).

In some embodiment, these polyether polyurethane films may have a durometer (Shore A) of about 88 psi (about 606.74 kPa), an ultimate tensile strength of about 8200 psi (56.54 MPa), and an ultimate elongation of 650%.

In some embodiments, the polymeric film may possess sufficient tensile strength to resist stretching under apposition forces created by negative-pressure therapy. The tensile strength of a material is the ability of material to resist stretching as represented by a stress-strain curve where stress is the force per unit area, i.e., Pascals (Pa), newtons per square meter ($N/m^2$), or pounds per square inch (psi). The ultimate tensile strength (UTS) is the maximum stress the material can withstand while being stretched before failing or breaking. Many materials display a linear elastic behavior defined by a linear stress-strain relationship often extending up to a nonlinear region represented by the yield point, i.e., the yield strength of a material. For example, high density polyethylene (HDPE) has a high tensile strength and low-density polyethylene (LDPE) has a slightly lower tensile strength, which are suitable materials for the sheets of non-porous, polymeric film as set forth above. Linear low density polyethylene (LLDPE) may also be suitable for some examples because the material stretches very little as the force is increased up to the yield point of the material. Thus, the standoffs 380 or other support features can be configured to resist collapsing (or stretching) when subjected to an external force or pressure. For example, HDPE has a UTS of about 37 MPa and may have a yield strength that ranges from about 26-33 MPa depending on the thickness of the material, while LDPE has somewhat lower values.

In some example embodiments, one or more of the first layer 315, the second layer 320, and the spacer layer 375 may comprise or consist essentially of a thermoplastic polyurethane (TPU) film that is permeable to water vapor but impermeable to liquid. The film may be in various degrees breathable and may have MVTRs that are proportional to their thickness. For example, the MVTR may be at least 300 $g/m^2$ per twenty-four hours in some embodiments. For permeable materials, the permeability generally should be low enough to maintain a desired negative pressure for the desired negative-pressure treatment.

In some example embodiments, the thermoplastic polyurethane film may be, for example, a Platilon® thermoplastic polyurethane film available from Convestro LLC, which may have a UTS of about 60 MPa and may have a yield strength of approximately 11 MPa or greater than about 10 MPa depending on the thickness of the material. Therefore, in some example embodiments, it is desirable that the non-porous, polymeric film may have a yield strength greater than about 10 MPa, depending on the type and thickness of material. A material having a lower yield strength may be too stretchable and, therefore, more susceptible to breaking with the application of small amounts of compression and/or apposition forces.

Figure 3C:
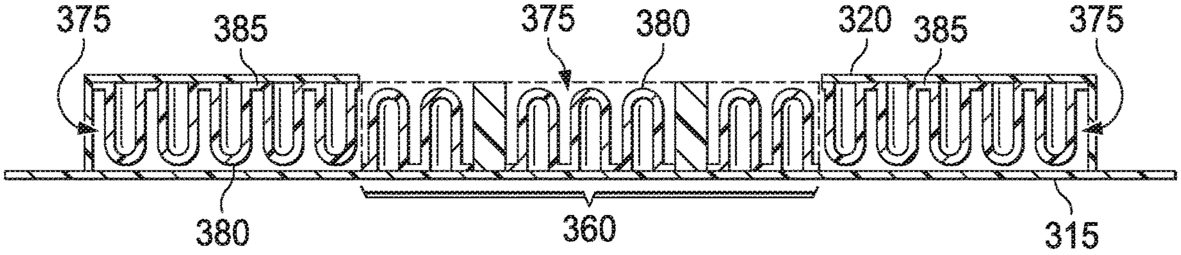
FIG. 3C is a schematic view of another example of an applicator that may be associated with some embodiments of the bridge of FIG. 3A.

FIG. 3C is a schematic view of another example of the applicator 240, illustrating details that may be associated with some embodiments. In the example of FIG. 3C, the applicator 240 has more than one spacer layer 375. At least some of the support features may be formed by sealing the base 385 of at least one of the spacer layers 375 to the second layer 320. Some of the supports 365 may extend from the second layer 320 toward the first layer 315 around the recessed space 360. In the example of FIG. 3C, all of the supports 365 around the recessed space 360 extend from the second layer 320 toward the first layer 315. At least some of the supports 365 may also extend from the first layer 315 toward the aperture 355 in the recessed space 360.

Figure 3D:
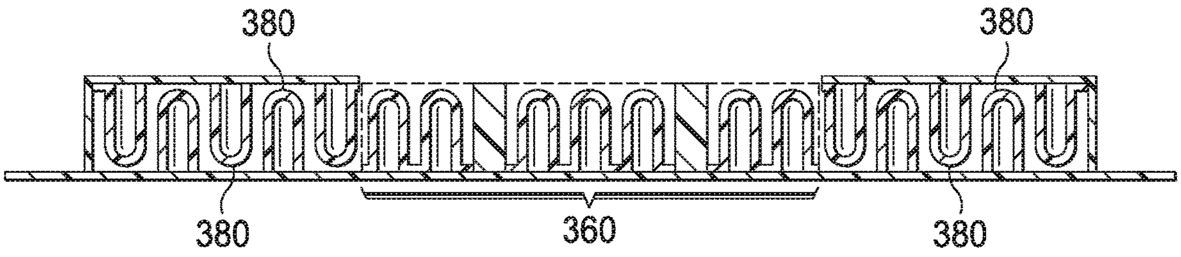
FIG. 3D is a schematic view of another example of an applicator that may be associated with some embodiments of the bridge of FIG. 3A.

FIG. 3D is a schematic view of another example of the applicator 240, illustrating additional details that may be associated with some embodiments. In the example of FIG. 3D, some of the supports 365 around the recessed space 360 extend from the second layer 320 toward the first layer 315, and some of the supports 365 around the recessed space 360 also extend from the first layer 315 toward the second layer 320. Some of the supports 365 also extend from the first layer 315 toward the aperture 355 in the recessed space 360.

Figure 4A:
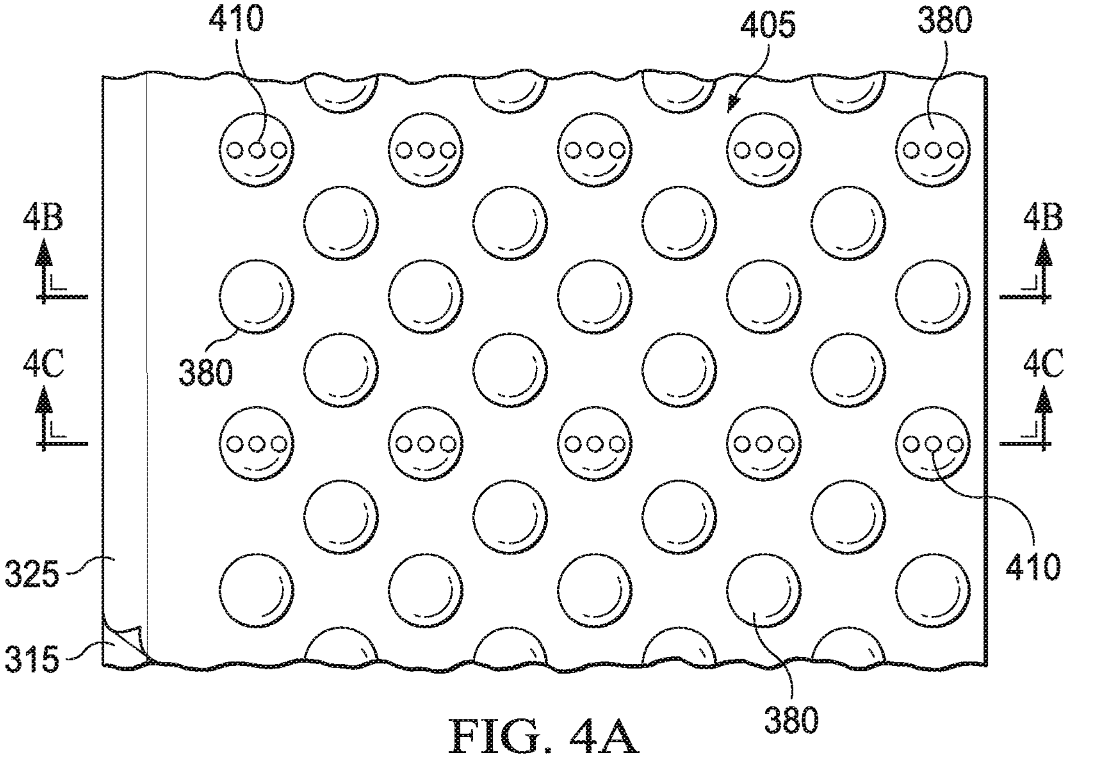
FIG. 4A is a schematic view of additional details that may be associated with various examples of support features in a bridge.

FIG. 4A is a schematic view of additional details that may be associated with various examples of support features in the bridge 160. For example, FIG. 4A illustrates a sealed region 405 between the standoffs 380. In some embodiments, the sealed region 405 may be formed by sealing portions of the spacer layer 375 to the first layer 315 or the second layer 320. In the example of FIG. 4A, the sealed region 405 may be formed by sealing the base 385 to the first layer 315 around the standoffs 380. As illustrated in the example of FIG. 4A, the standoffs 380 may have a circular edge proximate to the sealed region 405. In other embodiments, the standoffs 380 may have edges with other suitable shapes, such as rectangular, triangular, or hexagonal, or some combination of shapes. Additionally or alternatively, one or more of the standoffs 380 may be embossed with projections or nodes, such as the nodes 410 illustrated in the example of FIG. 4A.

The standoffs 380 in adjacent rows or columns may be staggered so that the standoffs 380 may be nested or packed together, as illustrated in the example of FIG. 4A. In other embodiments, the standoffs 380 may be arranged in other patterns suitable for the particular therapy being utilized. For example, the rows and columns of the standoffs 380 may be arranged in line to form an aligned, rectangular pattern so that there is more spacing between the standoffs 380. Increasing the spacing between the standoffs 380 may increase fluid flow within the fluid pathways of the bridge 160, whereas a nested arrangement may restrict fluid flow within the fluid pathways. For example, the standoffs 380 can be aligned to increase fluid flow of negative pressure being applied to a tissue interface and facilitate the removal of fluids and exudates within the recessed space 360. A nested pattern can facilitate pressure sensing within the recessed space 360 while impeding the inflow of fluids and exudates, which can reduce the possibility of blockage.

In some embodiments, distribution of the standoffs 380 may be characterized by a pitch, which can be defined by the center to center distance between each of the standoffs 380. For example, a pitch of about 1 mm to about 10 mm may be suitable for some configurations. In some embodiments, the pitch may be between about 2 mm and about 3 mm. Because the sealed region 405 can define an end of the standoffs 380, including a diameter of a circular end, and the pitch of the standoffs 380, the area of the spacer layer 375 having the standoffs 380 may also be determined as a percentage. For example, if each of the standoffs 380 has a diameter of about 1.0 mm and the pitch is about 2.0 mm, the coverage percentage is about 22% of the area of the spacer layer 375. In another example, if the diameter of each of the standoffs 380 is about 2.0 mm and the pitch is about 5.0 mm, the coverage percentage is about 14% of the area of the spacer layer 375. In yet another example, if the diameter of each of the standoffs 380 is about 1.5 mm, the pitch is about 2.0 mm, and the standoffs 380 are more tightly arranged such that there are about 28.5 standoffs in a 10 $mm^2$ section of the spacer layer 375, the coverage percentage is about 51% of the area of the spacer layer 375. Depending on the diameter, pitch, and arrangement of the standoffs 380, the coverage percentage may range between about 10% and about 60% of the surface area of the spacer layer 375. Support features having other shapes also may have a coverage percentage in generally the same range.

The size and pitch of the standoffs 380 also may be varied to effect change in the fluid flows through the fluid passageways. For example, the diameter and pitch of the standoffs 380 can be increased to increase fluid flow of negative pressure being applied to a tissue interface and facilitate the removal of fluids and exudates within the recessed space 360. The diameter, pitch, or both may be decreased to restrict fluid flow, which can reduce blockages, and facilitate pressure sensing within the recessed space 360.

Figure 4B:
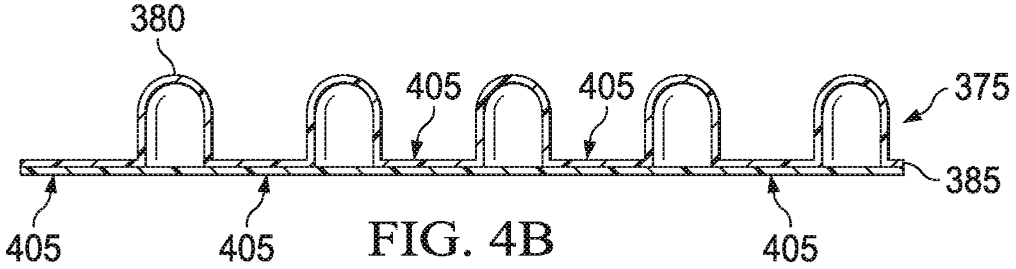
FIG. 4B is a schematic view of the support features of FIG. 4A taken along section 4B-4B, illustrating additional details that may be associated with some examples.

FIG. 4B is a schematic view of the support features of FIG. 4A taken along section 4B-4B, illustrating additional details that may be associated with some examples. In some embodiments, the standoffs 380 may have a hemispherical profile, as illustrated in the example of FIG. 4B. In other example embodiments, the standoffs 380 may be profiles that are conical, cylindrical, tubular having a flattened or hemispherical end, or geodesic. The standoffs 380 may be tubular in some embodiments, formed with generally parallel walls extending from the base 385 to a hemispherical or flat top portion of the standoffs 380. Alternatively, the walls of the standoffs 380 may taper or expand outwardly from the base 385. In some embodiments, the standoffs 380 that are generally hemispherical or tubular in shape may have a diameter between about 1.0 mm and about 10 mm. In some other embodiments, the standoffs 380 may have a diameter between about 2.0 mm and about 5.0 mm.

Figure 4C:
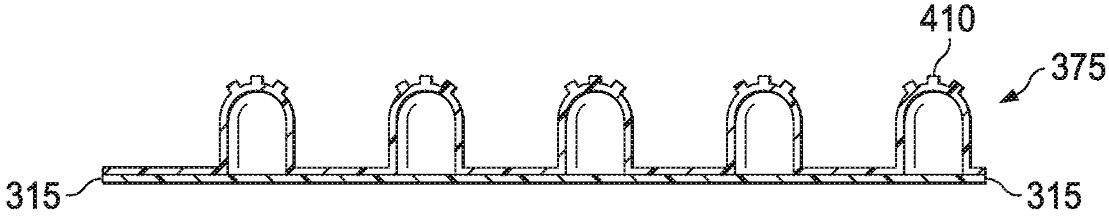
FIG. 4C is a schematic view of the example support features of FIG. 4A taken along section 4C-4C, illustrating additional details that may be associated with some embodiments.

FIG. 4C is a schematic view of the example support features of FIG. 4A taken along section 4C-4C, illustrating additional details that may be associated with some embodiments. In the example of FIG. 4C, the nodes 410 can be configured to contact the tissue interface 120 to enhance fluid flow to a tissue site. The nodes 410 may be flexible or rigid. In some embodiments, the nodes 410 may be formed from a substantially gas impermeable material, such as silicone. In other embodiments, the nodes 410 may be formed from a semi-gas permeable material. The nodes 410 may be formed from the same material as the spacer layer 375, and may be an integral part of the spacer layer 375. In some embodiments, the nodes 410 may be solid, while in other embodiments the projections may be hollow to increase flexibility. The nodes 410 may form a plurality of channels and/or voids to distribute reduced pressure and allow for fluid flow among the nodes 410. The nodes may be dimensioned to provide local load points evenly distributed at a tissue interface. The pattern and position of the nodes 410 may be uniform or non-uniform. The nodes may have different profiles, including, for example, the shape of a spike, cone, pyramid, dome, cylinder or rectangle.

Figure 5A:
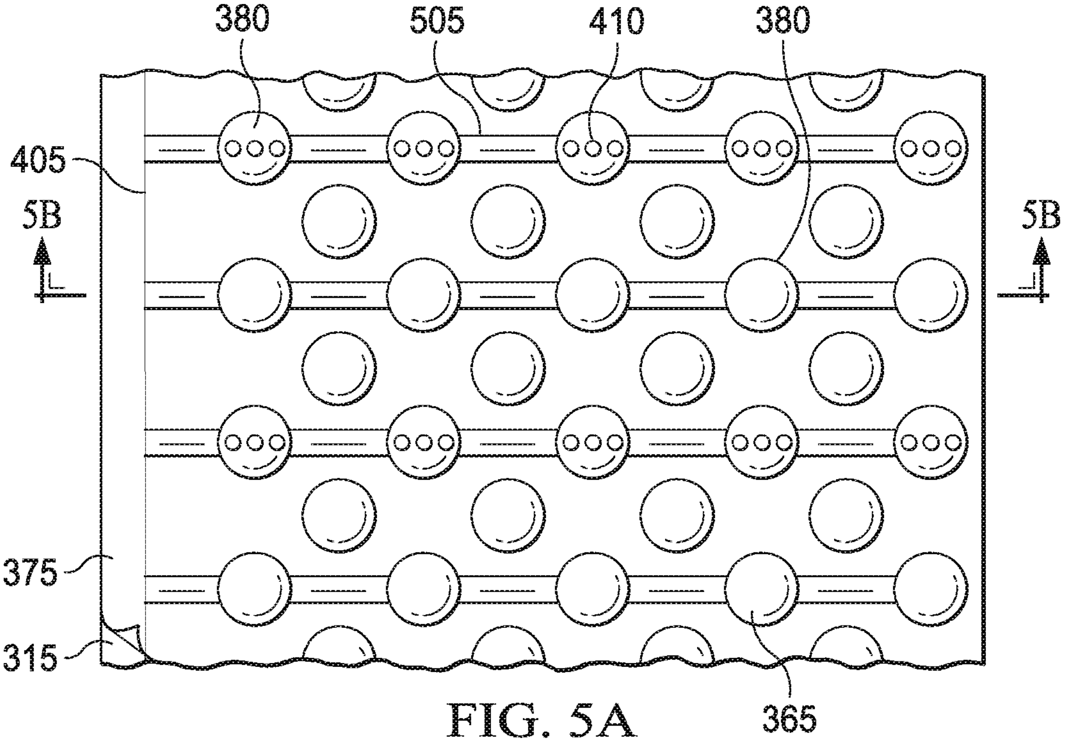
FIG. 5A is a schematic view of additional details that may be associated with some embodiments of a bridge in the therapy system of FIG. 1.

FIG. 5A is a schematic view of additional details that may be associated with some embodiments of the bridge 160. For example, in FIG. 5A one or more passageways 505 may be formed between the supports 365.

Figure 5B:
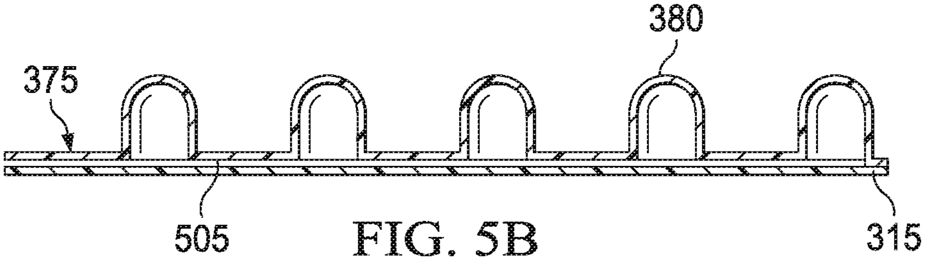
FIG. 5B is a schematic view taken along section 5B-5B of FIG. 5A, illustrating additional details that may be associated with some embodiments.

FIG. 5B is a schematic view taken along section 5B-5B of FIG. 5A, illustrating additional details that may be associated with some embodiments. For example, as seen in FIG. 5B, at least some of the standoffs 380 may be fluidly coupled through the passageways 505. The passageways 505 and the standoffs 380 can form a closed chamber. In some examples, a closed chamber may be formed by all of the standoffs 380 in a row fluidly coupled by the passageways 505 as shown in FIG. 5A and FIG. 5B. The closed chambers may be formed in alternating rows as also shown in FIG. 5A. The formation of closed chambers with the standoffs 380 can distribute apposition forces more equally.

Figure 6A:
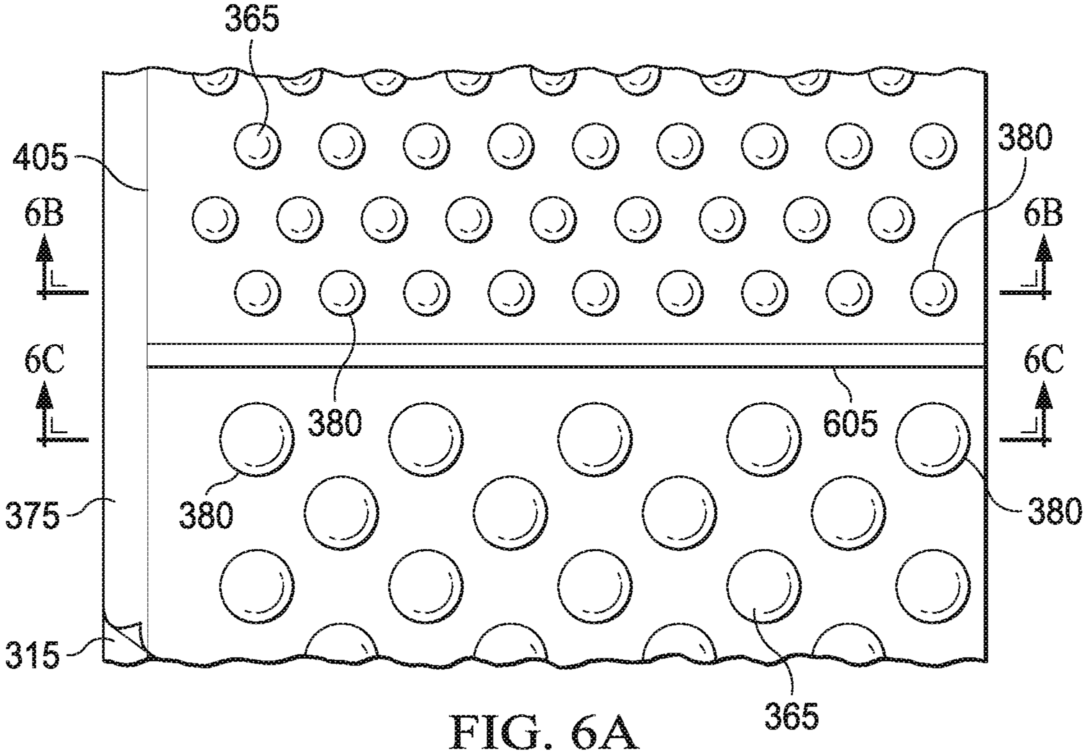
FIGS. 6A, 6B, and 6C illustrate other examples of features that may be associated with some embodiments of a bridge in the therapy system of FIG. 1.
Figure 6B:
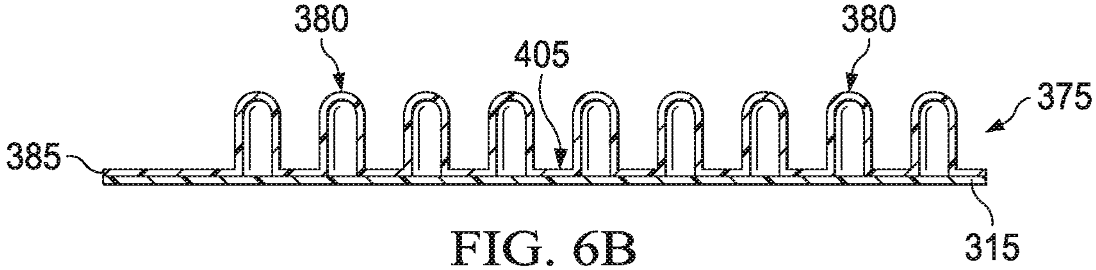
Figure 6C:
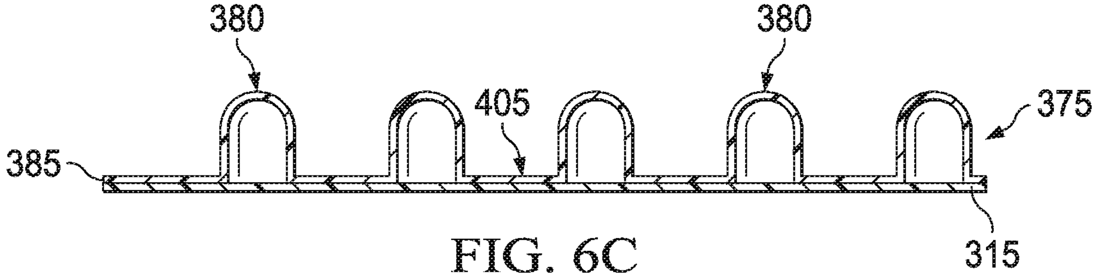

FIGS. 6A, 6B, and 6C illustrate other examples of features that may be associated with some embodiments of the bridge 160. In FIG. 6A, the first layer 315 and the spacer layer 375 define a nested arrangement of the supports 365. The example of FIG. 6A further illustrates that at least some of the supports 365 may additionally or alternatively have different sizes. For example, some of the supports 365 may have a diameter in the range between about 1 mm and about 10 mm, and some of the supports 365 may have a diameter in the range between about 1 mm and about 3 mm. In some embodiments, a wall 605 may be disposed between the some of the supports 365. For example, the wall 605 in the example of FIG. 6A is disposed between the supports 365 having different sizes. The supports 365 having a larger diameter and pitch may increase fluid flow to facilitate the removal of fluids and exudates within the recessed space 360 in some embodiments. In some embodiments, the supports 365 having a smaller diameter and pitch may restrict fluid flow to facilitate pressure sensing within the recessed space 360 while impeding the inflow of fluids and exudates into the first pathway 340. The arrangement and dimensions of the supports 365 may be tailored to manage the delivery of negative pressure to the tissue interface 120 and the measurement of pressure within the recessed space 360.

Figure 7:
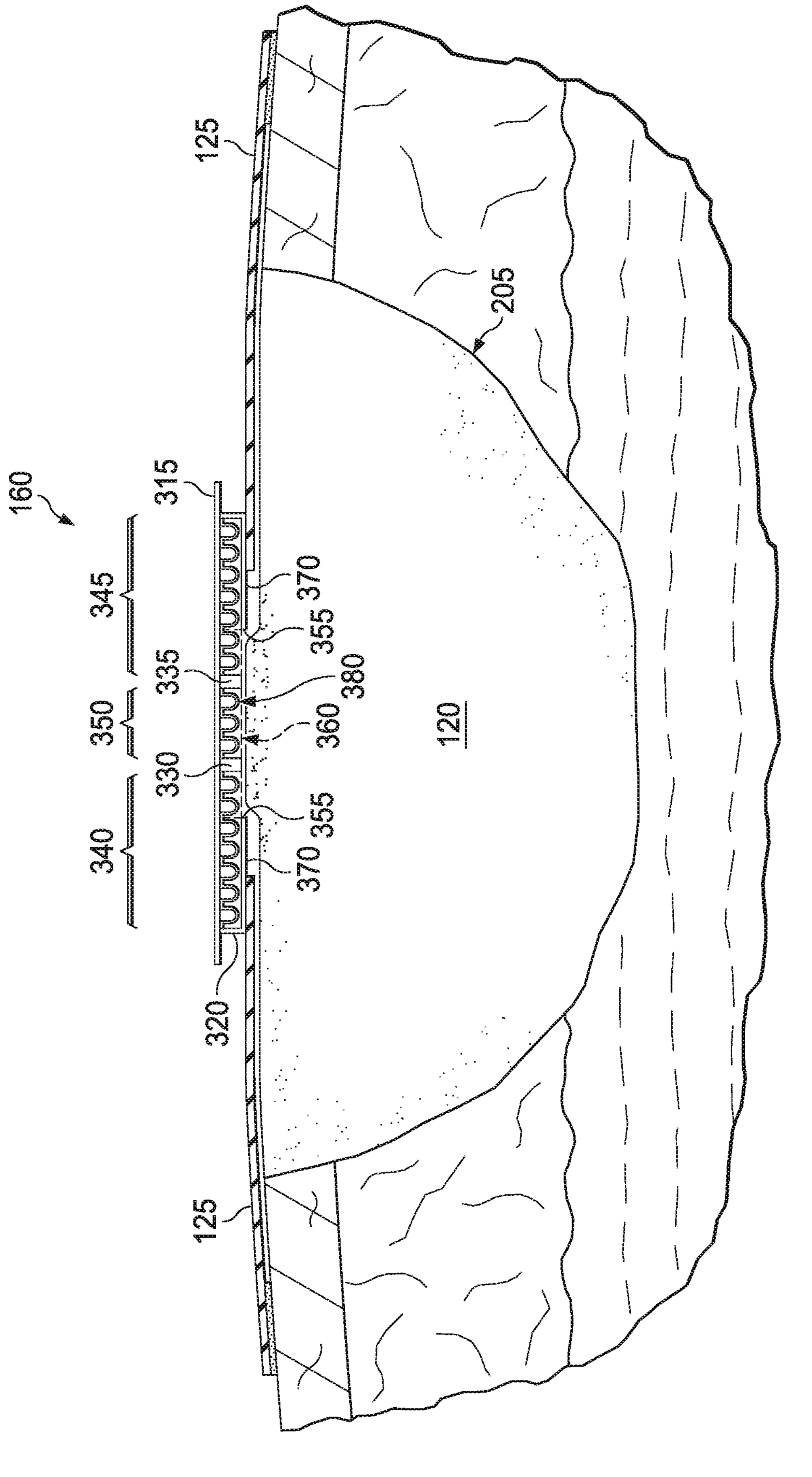
FIG. 7 is a schematic diagram of the bridge of FIG. 3A applied to a tissue site with negative pressure.

FIG. 7 is a schematic diagram of the bridge 160 of FIG. 3A applied to the tissue site 205 with negative pressure. The tissue interface 120 may be in fluid communication with the recessed space 360 through the aperture 355. The affixation surface 370 may be coupled to the cover 125 to seal and fluidly couple the recessed space 360 to the tissue interface 120. In the example of FIG. 7, the first wall 330 and the second wall 335 partially define the first pathway 340, the second pathway 345, and the third pathway 350 between the first layer 315 and the second layer 320.

Within the recessed space 360, the standoffs 380 can extend from the first layer 315 toward the tissue interface 120 and may be adapted to come in direct contact with the tissue interface 120 if negative pressure is applied to the bridge 160. Negative pressure can compress the bridge 160, and the first layer 315 and the second layer 320 can collapse toward each other because of the vacuum created within the standoffs 380. Although the standoffs 380 may change shape or flatten somewhat under negative pressure, the volume of the standoffs 380 remains substantially constant and can maintain fluid flow through the third pathway 350. The standoffs 380 can also provide a cushion to help prevent the sealed spaces of the bridge 160 from collapsing as a result of external forces. The standoffs 380 disposed in the third pathway 350 may be sized and arranged in a pattern that may increase fluid flow of negative pressure being applied to the tissue interface 120 to facilitate the removal of fluids and exudates within the recessed space 360. The standoffs 380 disposed in the first pathway 340 and the second pathway 345 may be sized and arranged in a pattern to facilitate pressure sensing within the recessed space 360 while impeding the inflow of fluids and exudates into the first pathway 340 and the second pathway 345 to reduce blockage conditions.

The standoffs 380 may have a variety of shapes, and may be sized and arranged in different patterns within the sealed space to enhance the delivery of negative pressure to the tissue interface 120 for a specific type of tissue site while optimizing pressure sensing and measurement of the negative pressure within the recessed space 360.

Figure 8:
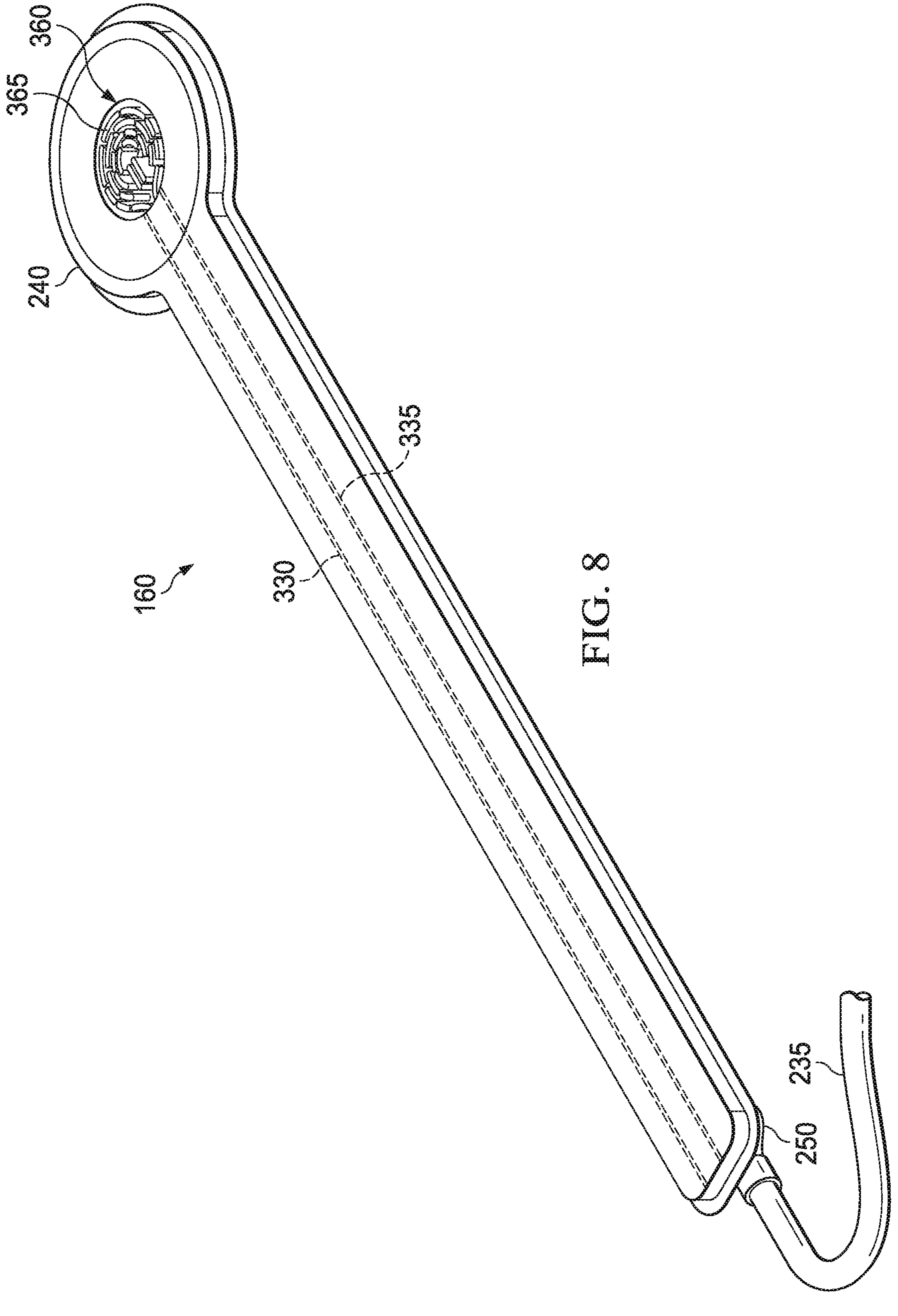
FIG. 8 is a perspective bottom view of another example of a bridge that may be associated with some embodiments of the therapy system of FIG. 1.

FIG. 8 is a perspective bottom view of another example of the bridge 160 having a low-profile structure that may be associated with some embodiments of the therapy system 100. As illustrated in the example of FIG. 8, the first wall 330 and the second wall 335 may extend lengthwise through the bridge 160 between the recessed space 360 and the adapter 250.

Figure 9A:
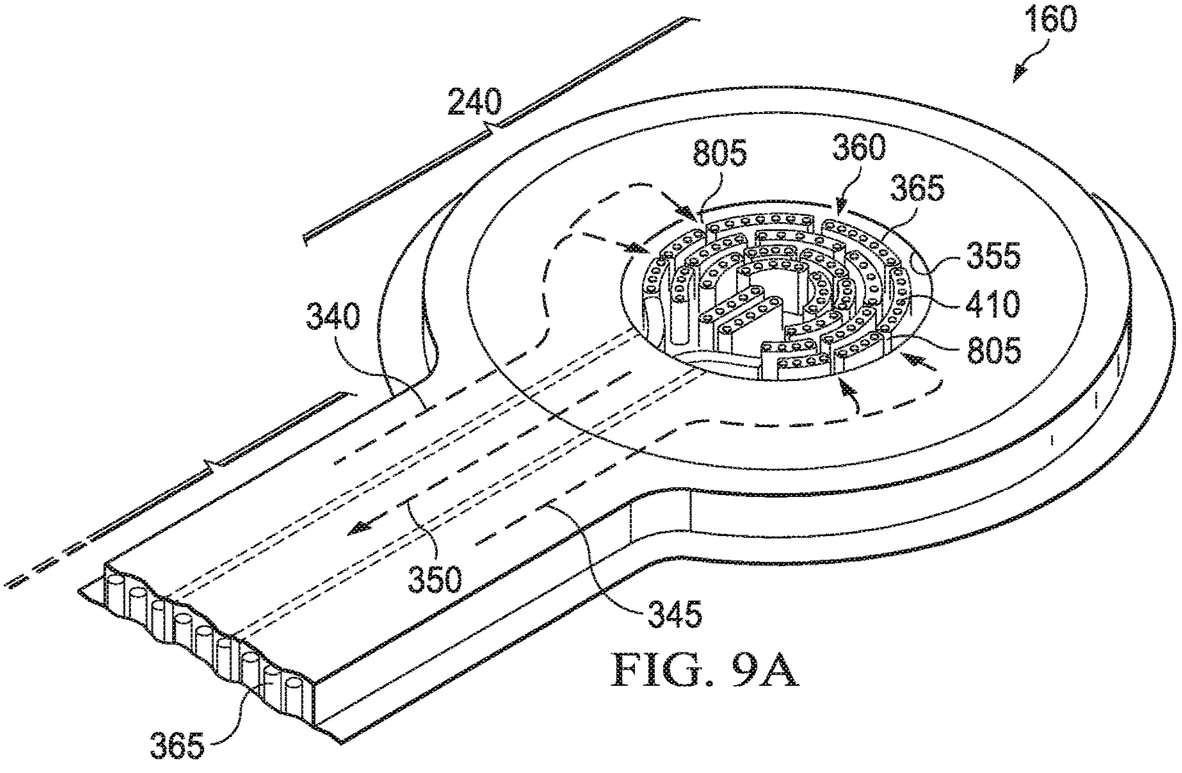
FIG. 9A and FIG. 9B are segmented perspective views of the bridge of FIG. 8.
Figure 9B:
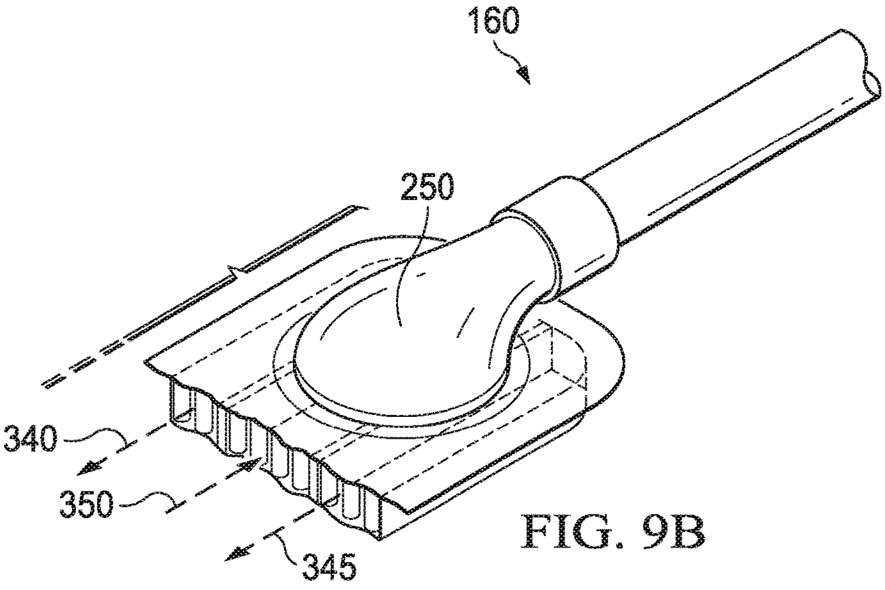

FIG. 9A and FIG. 9B are segmented perspective views of the bridge 160 of FIG. 8, illustrating additional details that may be associated with some examples. FIG. 9A is a bottom perspective view of an example of the applicator 240, illustrating a configuration having a circular profile. FIG. 9B is a top perspective view of an example of the adapter 250, which may have an elbow connector of semi-rigid material in some embodiments.

The aperture 355 of FIG. 9A is generally circular and opens to the recessed space 360. The supports 365 of FIG. 9A may have a generally elongated and arcuate profile and may be arranged in a generally concentric pattern within the recessed space 360. Some embodiments of the supports 365 may also comprise surface features, such as the nodes 410. The supports 365 disposed in the center of the recessed space 360 may be more aligned with the third pathway 350 to increase fluid flow of negative pressure being applied to the tissue interface 120 and facilitate the removal of fluids and exudates within the recessed space 360. In some embodiments, some of the supports 365 may be disposed around the aperture 355 to form a semicircular path opposite the third pathway 350, including spaces or gaps 805 between the supports 365. The semicircular alignment of the supports 365 may be positioned within the recessed space 360 to minimize contact with the flow of fluids passing through from the tissue interface 120 to the third pathway 350 if negative pressure is applied. Additionally, the gaps 805 may be sufficiently small for further restricting fluid flow into the first pathway 340 and the second pathway 345, as indicated by the dashed arrows. The gaps 805 can facilitate pressure sensing within the recessed space 360 while impeding the inflow of fluids and exudates into the first pathway 340 and the second pathway 345 to reduce the possibility of blockage. In some embodiments, a portion of the perimeter of the aperture 355 may be welded to an outer ring of the supports 365 to further restrict fluid flow to the first pathway 340 and the second pathway 345 and further impede the inflow of fluids and exudates without inhibiting pressure sensing within the recessed space 360.

Figure 10:
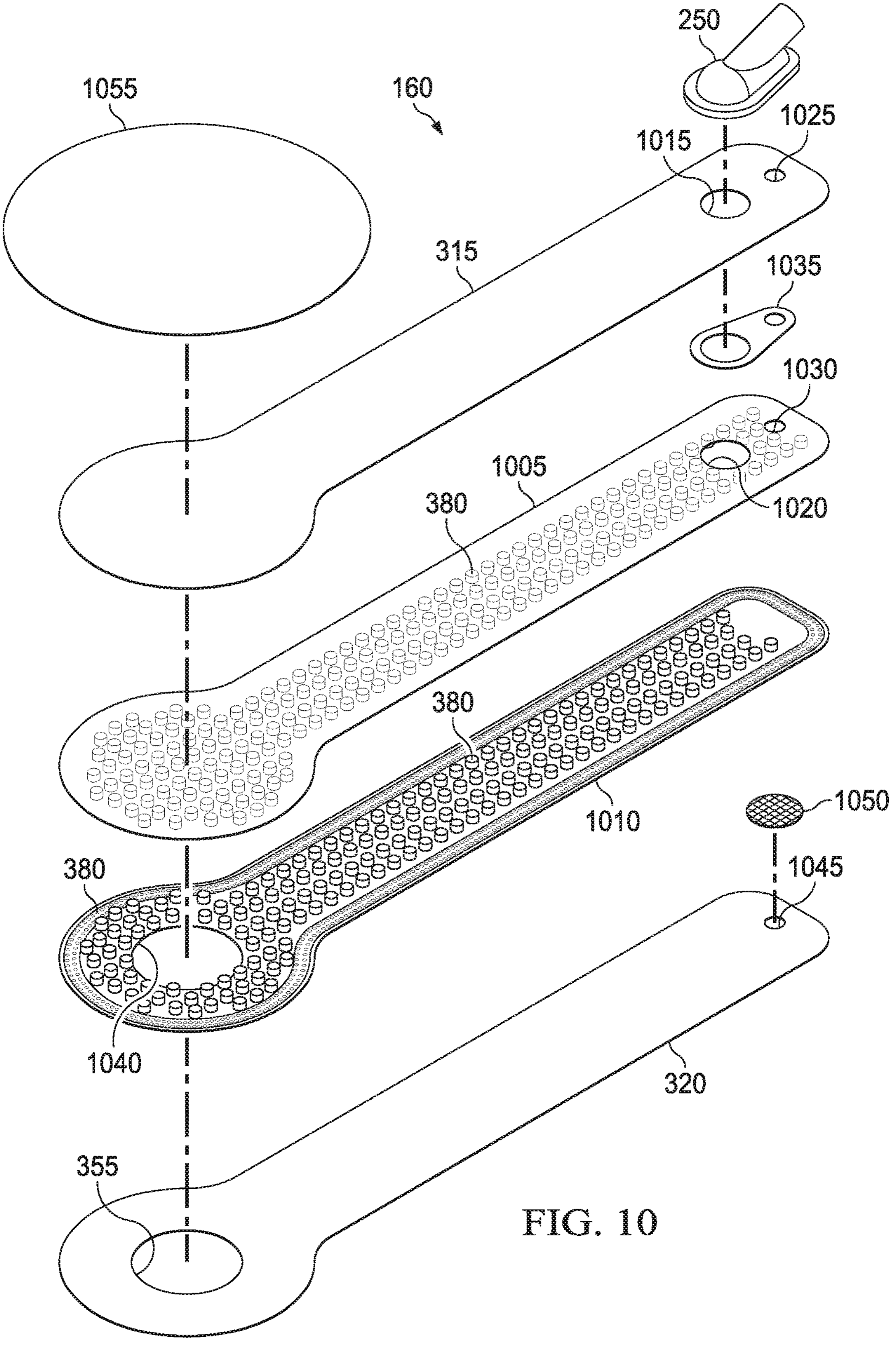
FIG. 10 is an assembly view of another example of a bridge that may be associated with some example embodiments of the therapy system of FIG. 1.

FIG. 10 is an assembly view of another example of the bridge 160 having a low-profile structure that may be associated with some embodiments of the therapy system 100. As illustrated in the example of FIG. 10, the bridge 160 comprises two spacer layers—a spacer layer 1005 and a spacer layer 1010—disposed between the first layer 315 and the second layer 320. Standoffs 380 may be formed in each of the spacer layer 1005 and the spacer layer 1010. In the example of FIG. 10, the standoffs 380 in the spacer layer 1005 are configured to extend toward the spacer layer 1010, and the standoffs 380 in the spacer layer 1010 are configured to extend toward the spacer layer 1005. The first layer 315 may have a passage 1015, and the spacer layer 1005 may have a passage 1020, through which fluids may flow to the adapter 250. The passage 1015 may be concentric with the passage 1020. The first layer 315 and the spacer layer 1005 may additionally have a passage 1025 and a passage 1030, respectively, which may also be fluidly coupled to the adapter 250. The passage 1025 may be concentric with the passage 1030. The bridge 160 may further comprise a fluid exit bond 1035, which can prevent leakage of fluids flowing through the passage 1015 and the passage 1020. The spacer layer 1010 may further have an aperture 1040 concentric with the aperture 355 of the second layer 320. The second layer 320 may have an aperture 1045. In some embodiments, the aperture 1045 may have a diameter in a range of about 0.01 millimeters to about 2.5 millimeters. In some embodiments, the aperture 1045 may have a diameter less than 0.01 millimeters. In some embodiments, the aperture 1045 may have a diameter greater than 2.5 millimeters. A hydrophobic filter 1050 may be disposed over the aperture 1045.

As further shown in FIG. 10, the passage 1015 and the passage 1025 may be located proximate a first end of the first layer 315, the passage 1020 and the passage 1030 may be located proximate a first end of the spacer layer 1005, the aperture 1040 may be located proximate a second end of the spacer layer 1010, the aperture 1045 may be located proximate a first end of the second layer 320, and the aperture 355 may be located proximate a second end of the second layer 320.

In some embodiments, the second layer 320 may be a film having a high MVTR in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties. In some embodiments, the second layer 320 may comprise or consist essentially of a polymer film, such as Inspire 2301 and Inpsire 2304 polyurethane films, commercially available from Expopack Advanced Coatings, Wrexham, United Kingdom. In some embodiments, the second layer 320 may comprise INSPIRE 2301 having an MVTR (upright cup technique) of 2600-2700 $g/m^2/24$ hours and a thickness of about 30 microns. In some embodiments, the second layer 320 may comprise INSPIRE 2304 having an MVTR (upright cup technique) of 2600 $g/m^2/24$ hours and a thickness of about 30 microns. The second layer 320 may be oriented to permit moisture-vapor transmission through the second layer 320 toward the first layer 315.

In some embodiments, a bridge cover 1055 may provide additional protection and support over a portion of the bridge 160. In some embodiments, the bridge cover 1055 may also cover any adhesive that might be exposed after applying the bridge 160 to a tissue site. In some embodiments, the bridge cover 1055 may be similar or analogous to the cover 125. For example, the bridge cover 1055 may be a polymer, such as a polyurethane film.

Figure 11A:
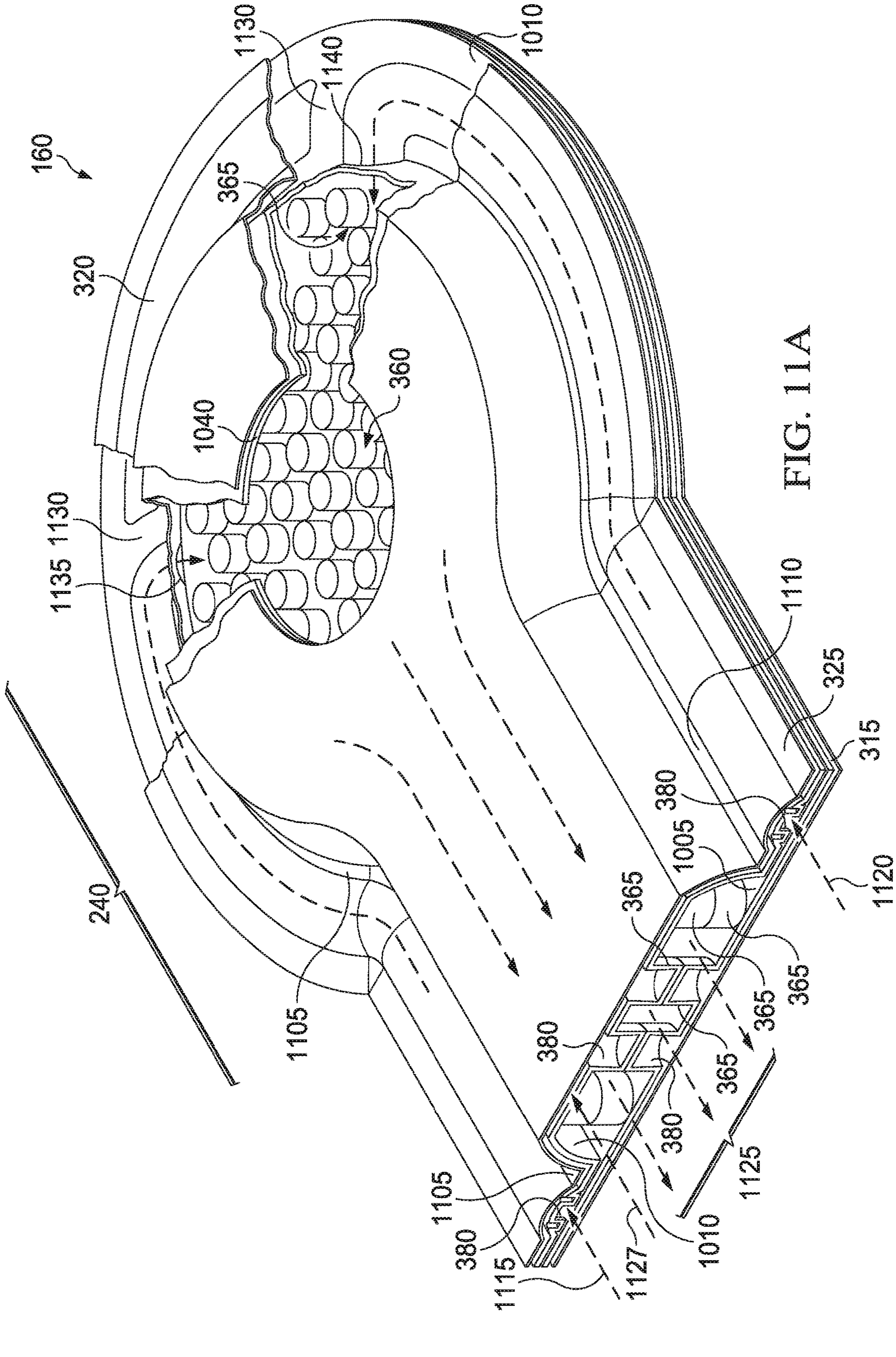
FIG. 11A is a segmented view of an assembled portion of the bridge in the example of FIG. 10, illustrating additional details that may be associated with some embodiments.

FIG. 11A is a segmented view of an assembled portion of the bridge 160 in the example of FIG. 10, illustrating additional details that may be associated with some embodiments. As illustrated in the example of FIG. 11A, the first layer 315, second layer 320, the spacer layer 1005, and the spacer layer 1010 may be assembled in a stacked relationship. For example, the first layer 315 may be coupled to the spacer layer 1005, the second layer 320 may be coupled to the spacer layer 1010, and a periphery of the spacer layer 1005 may be coupled to a periphery of the spacer layer 1010 to form the flange 325. The spacer layer 1005 and the spacer layer 1010 can be coupled to form a liquid barrier defining a fluid path along a longitudinal axis of the bridge 160.

Some embodiments of the bridge 160 may additionally comprise at least one barrier or wall, such as a first wall 1105, interior to the flange 325. The first wall 1105 may be formed by coupling the spacer layer 1005 and the spacer layer 1010. For example, the spacer layer 1005 may be welded to the spacer layer 1010 to form the first wall 1105. In some embodiments, the first wall 1105 may extend lengthwise through the bridge 160 into the applicator 240 to form at least two fluid paths between the spacer layer 1005 and the spacer layer 1010 within the bridge 160. In some examples, the bridge 160 may further comprise a second barrier, such as a second wall 1110. The second wall 1110 may be formed by coupling the spacer layer 1005 and the spacer layer 1010. In some embodiments, the second wall 1110 also may extend lengthwise through the bridge 160 into the applicator 240. In some example embodiments, the first wall 1105 and the second wall 1110 may comprise a polymeric film coupled between the first layer 315 and the second layer 320. In some other example embodiments, the first wall 1105 and the second wall 1110 may comprise a weld (RF or ultrasonic), a heat seal, an adhesive bond, or a combination of any of the foregoing.

In some embodiments, barriers or walls interior to the flange 325 may form fluid pathways between the spacer layer 1005 and the spacer layer 1010. For example, in FIG. 11A, the first wall 1105 and the second wall 1110 cooperate with the flange 325 to form a first fluid conductor 1115, a second fluid conductor 1120, a third fluid conductor 1125, and a fourth fluid conductor 1127. In some applications, the first fluid conductor 1115 and the second fluid conductor 1120 may be coupled to a sensor to measure pressure. The third fluid conductor 1125 may be coupled to a negative-pressure source and the fourth fluid conductor 1127 may be coupled to the third fluid conductor 1125 through the aperture 1040. In some example embodiments, the first fluid conductor 1115 and the second fluid conductor 1120 may have a height having a value in a range between about 0.25 mm and about 3 mm. In some example embodiments, the first fluid conductor 1115 and the second fluid conductor 1120 may have a width having a value in a range between about 1 mm and about 7.5 mm. Thus, the first fluid conductor 1115 and the second fluid conductor 1120 may have a cross-sectional area having a value in a range between about 0.17 $mm^2$ and 16.77 $mm^2$. In some embodiments, the first fluid conductor 1115 and the second fluid conductor 1120 may have a cross-sectional area having a value in a range between about 0.1 $mm^2$ and 18 $mm^2$.

In some examples, each of the first wall 1105 and the second wall 1110 may extend an angular distance around the proximal end of the applicator 240 and cooperate with blocking walls of the flange 325, such as blocking walls 1130, to form extensions of the first fluid conductor 1115 and the second fluid conductor 1120. The extensions may be fluidly coupled to the recessed space 360. In the example of FIG. 11A, the first fluid conductor 1115 and the second fluid conductor 1120 are fluidly coupled to the recessed space 360 through passages, such as a through-hole 1135 and a through-hole 1140, respectively. In some examples, at least some of the supports may be disposed in one or both of the first fluid conductor 1115 and the second fluid conductor 1120. For example, some of the supports may be formed by the standoffs 380 disposed between the flange 325 and the first wall 1105, and between the flange 325 and the second wall 1110. Additionally or alternatively, the thickness of the spacer layer 1010 may be increased to provide additional structural support to the first fluid conductor 1115 and the second fluid conductor 1120. In some examples, the first fluid conductor 1115 and the second fluid conductor 1120 may comprise or be formed by tubes through or along the bridge 160. Some configurations may not have the first fluid conductor 1115 or the second fluid conductor 1120, or may have only one of the first fluid conductor 1115 and the second fluid conductor 1120.

Each of the first wall 1105 and the second wall 1110 can extend at least partially around the proximal end of the applicator 240 that form the first fluid conductor 1115 and the second fluid conductor 1120. For example, in some embodiments each of the first wall 1105 and the second wall 1110 can extend from about 45° to about 315° from the center of the third fluid conductor 1125 where the third fluid conductor 1125 is in fluid communication with the recessed space 360. In some embodiments, the angular distance may be different for each of the first fluid conductor 1115 and the second fluid conductor 1120. For example, the angular distance for each of the first fluid conductor 1115 and the second fluid conductor 1120 may be about 60° and 210°, respectively, from the third fluid conductor 1125.

In some example embodiments, the through-hole 1135 and the through-hole 1140 may be separated from each other by an angular distance of at least 90°, extending around the applicator 240 in a direction away from the third fluid conductor 1125. The spacing and disposition of the through-hole 1135 and the through-hole 1140 from each other, and from the third fluid conductor 1125, can allow the first fluid conductor 1115 and the second fluid conductor 1120 to better avoid the flow of fluids passing through from the tissue interface 120 to the third fluid conductor 1125 when negative pressure is applied. Additionally, the through-hole 1135 and the through-hole 1140 may be sufficiently small for further restricting fluid flow into the first fluid conductor 1115 and the second fluid conductor 1120. In some embodiments, the through-hole 1135 and the through-hole 1140 may have a cross-sectional area having a value in a range between about 0.17 $mm^2$ and 16.77 $mm^2$. In some embodiments, the through-hole 1135 and the through-hole 1140 may have a cross-sectional area having a value in a range between about 0.1 $mm^2$ and 18 $mm^2$ to further restrict fluid flow to the first fluid conductor 1115 and the second fluid conductor 1120 and impede the inflow of fluids and exudates without inhibiting pressure sensing within the recessed space 360.

As further shown in FIG. 11A, in some examples, at least some of the supports 365 may be disposed in the third fluid conductor 1125. For example, some of the supports 365 may be formed by the standoffs 380 disposed between the first wall 1105 and the second wall 1110.

Figure 11B:
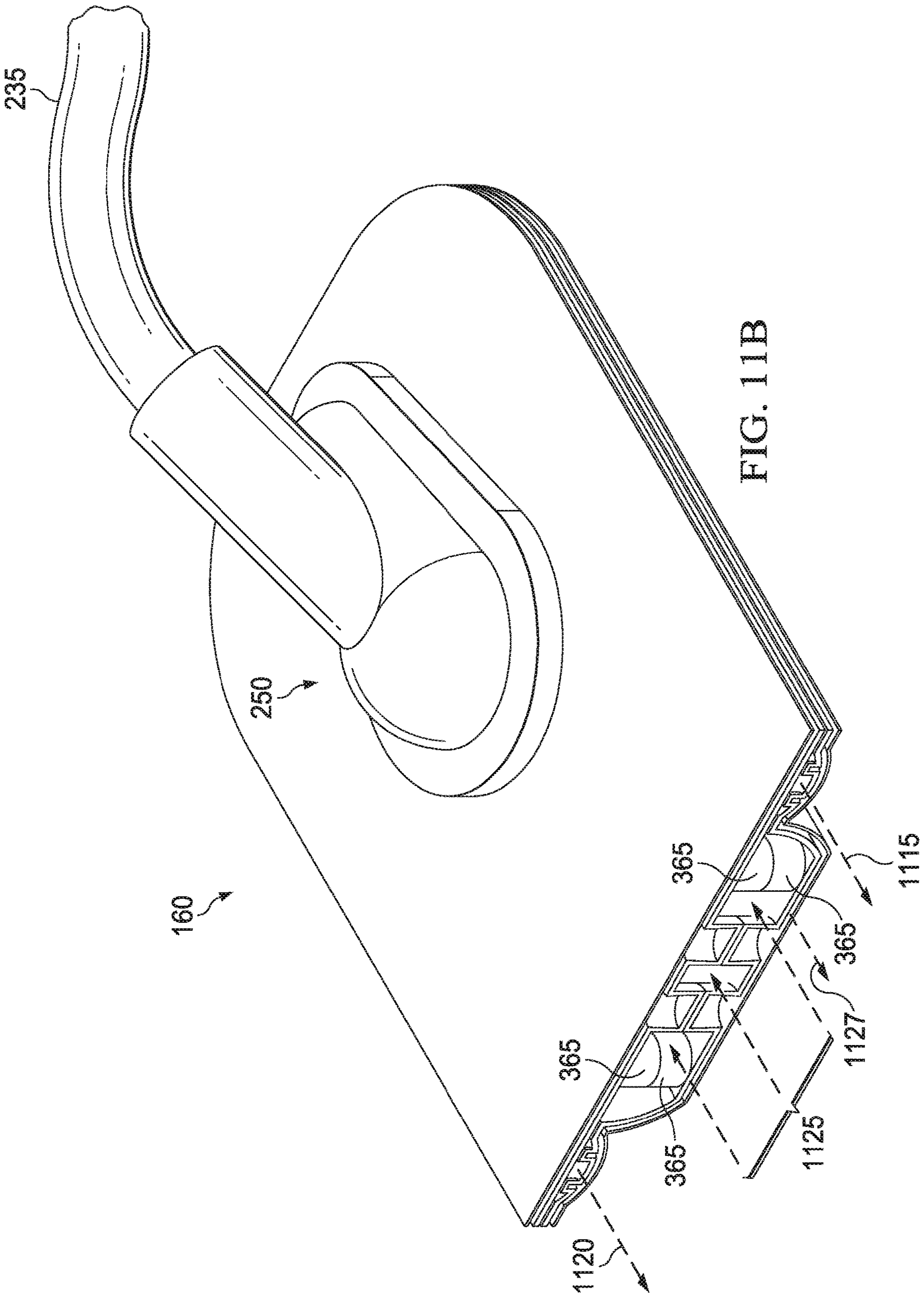
FIG. 11B is a segmented perspective view of portion of the bridge in the example of FIG. 10, illustrating additional details that may be associated with some embodiments.

FIG. 11B is a segmented perspective view of portion of the bridge 160 in the example of FIG. 10, illustrating additional details that may be associated with some embodiments. FIG. 11B further illustrates an example of the adapter 250 and the conduit 235 coupled to the bridge 160. Each of the first fluid conductor 1115 and the second fluid conductor 1120 may be fluidly coupled directly to the conduit 235 in some examples. In other examples, both of the first fluid conductor 1115 and the second fluid conductor 1120 may be fluidly coupled to a single space (not shown) within the adapter 250, which can be fluidly coupled to the conduit 235.

In the example of FIG. 11A and FIG. 11B, both the first fluid conductor 1115 and the second fluid conductor 1120 are fluidly separate from and parallel to the third fluid conductor 1125 and the fourth fluid conductor 1127. The parallel orientation can minimize the vertical profile of the bridge 160, while still being resistant to collapsing under pressure that could block fluid flow through the fluid pathways.

Figure 12A:
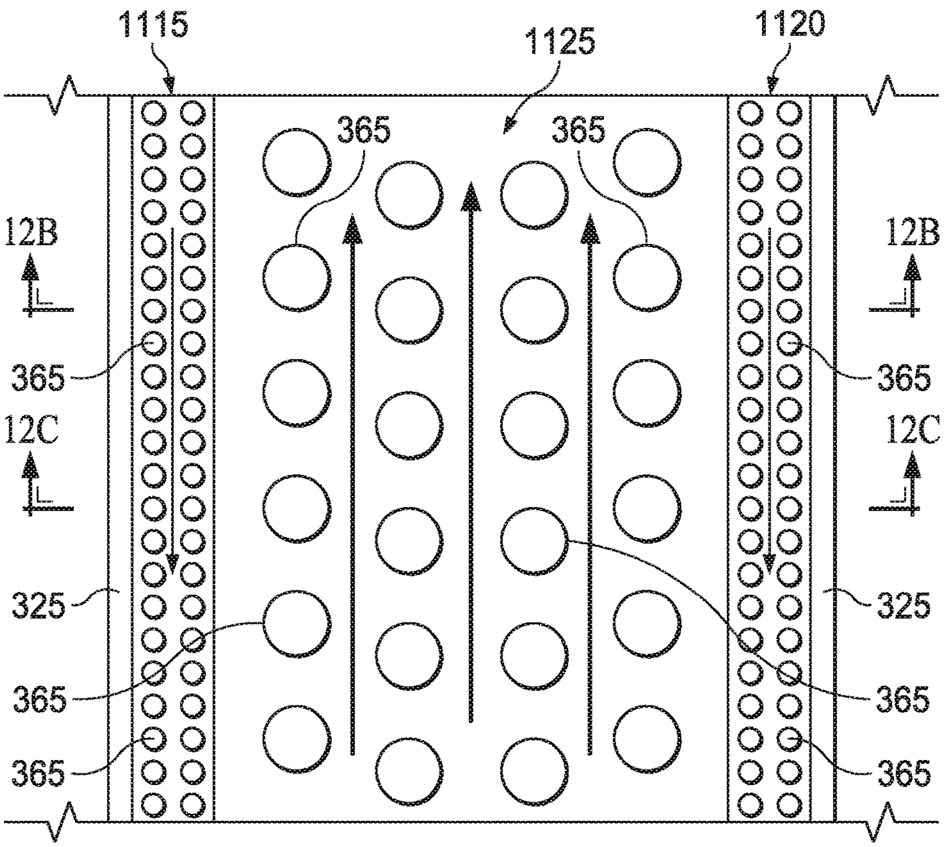
FIG. 12A is a schematic view of an example configuration of fluid pathways in the bridge of FIG. 10 as assembled, illustrating additional details that may be associated with some embodiments.
Figure 12B:
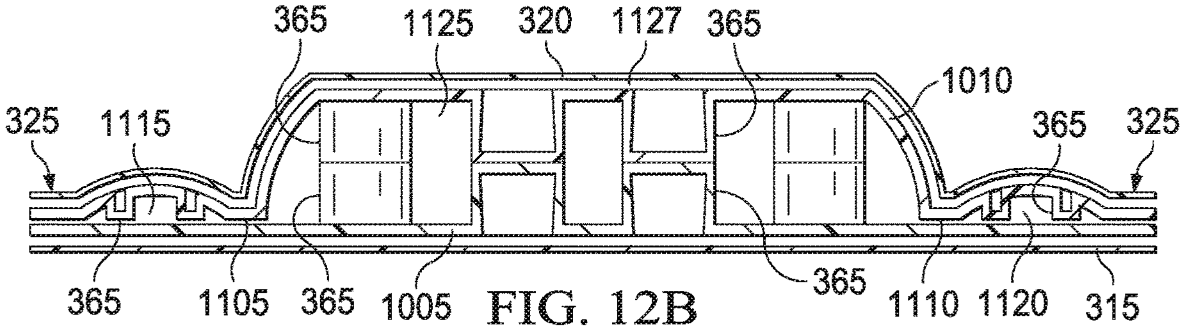
FIG. 12B is a schematic view taken along line 12B-12B of FIG. 12A.
Figure 12C:
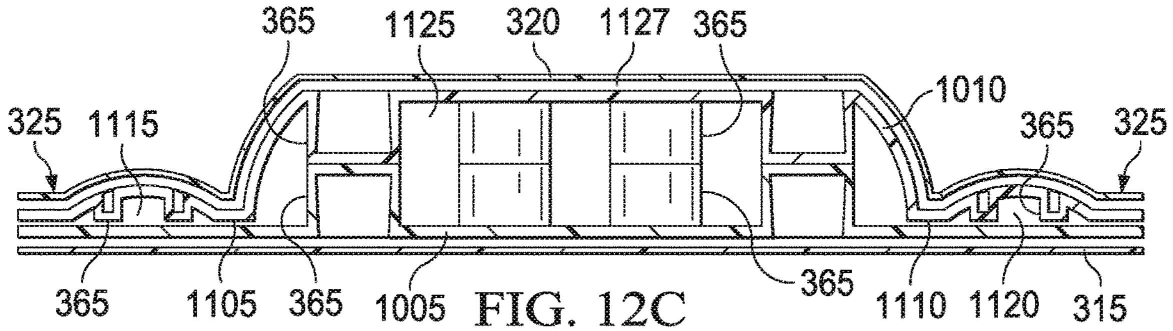
FIG. 12C is a schematic view taken along line 12C-12C of FIG. 12A.

FIG. 12A is a schematic view of an example configuration of fluid pathways in the bridge 160 of FIG. 10 as assembled, illustrating additional details that may be associated with some embodiments. In the example of FIG. 12A, the bridge 160 has four rows of the supports 365, and the supports 365 forming outside rows are offset or staggered from the supports 365 forming the two inside rows. FIG. 12B is a schematic view taken along line 12B-12B, and FIG. 12C is a schematic view taken along line 12C-12C. The supports 365 may have a variety of shapes, and may be sized and arranged in different patterns within the third fluid conductor 1125. For example, as illustrated in the examples of FIG. 12B and FIG. 12C, some of the supports 365 may extend from the spacer layer 1005 away from the first layer 315 and some of the supports 365 may extend from the spacer layer 1010 away from the second layer 320. In some embodiments, some of the supports 365 may be opposingly aligned. For example, at least some of the supports 365 can extend from the spacer layer 1005 towards some of the supports 365 extending from the spacer layer 1010, and some of the supports 365 in opposition may contact each other. In some embodiments, the bridge 160 may include more than one row of the supports 365. Each of the first wall 1105 and the second wall 1110 cooperate with the flange 325 to form the first fluid conductor 1115 and the second fluid conductor 1120. In some embodiments, some of the supports 365 may be disposed within one or both of the first fluid conductor 1115 and the second fluid conductor 1120. As further shown in FIG. 12B and FIG. 12C, the first wall 1105, the second wall 1110, the spacer layer 1010, and the second layer 320 may cooperate for form the fourth fluid conductor 1127. Thus, the fourth fluid conductor 1127 may be between the spacer layer 1010 and the second layer 320.

The supports 365 disposed in the third fluid conductor 1125 may have a larger diameter and pitch than the supports 365 in the first fluid conductor 1115 and the second fluid conductor 1120, and may increase fluid flow to facilitate the removal of fluids and exudates within the recessed space 360. The supports 365 in the first fluid conductor 1115 and the second fluid conductor 1120 may have a noticeably smaller diameter and pitch than the supports 365 in the third fluid conductor 1125, and may restrict fluid flow to facilitate pressure sensing within the recessed space 360 while impeding the inflow of fluids and exudates into the first fluid conductor 1115 and the second fluid conductor 1120. The arrangement and dimensions of the supports 365 may be tailored to manage the delivery of negative pressure to the tissue interface 120 and the measurement of pressure within the recessed space 360.

Figure 13A:
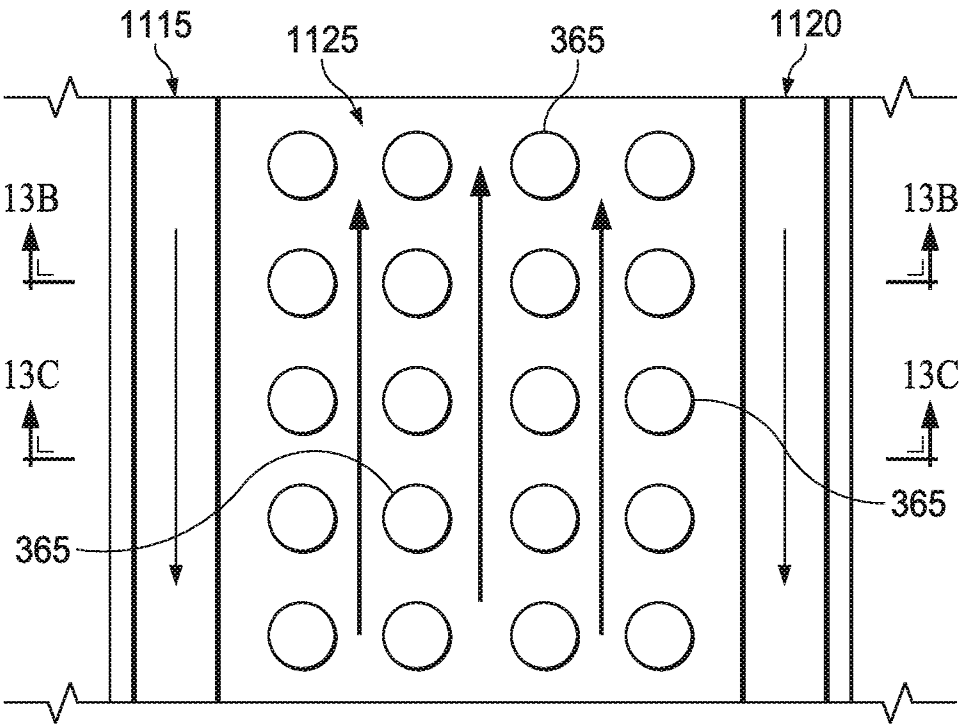
FIG. 13A is a schematic view of another example configuration of fluid pathways in the bridge of FIG. 10 as assembled, illustrating additional details that may be associated with some embodiments.
Figure 13B:
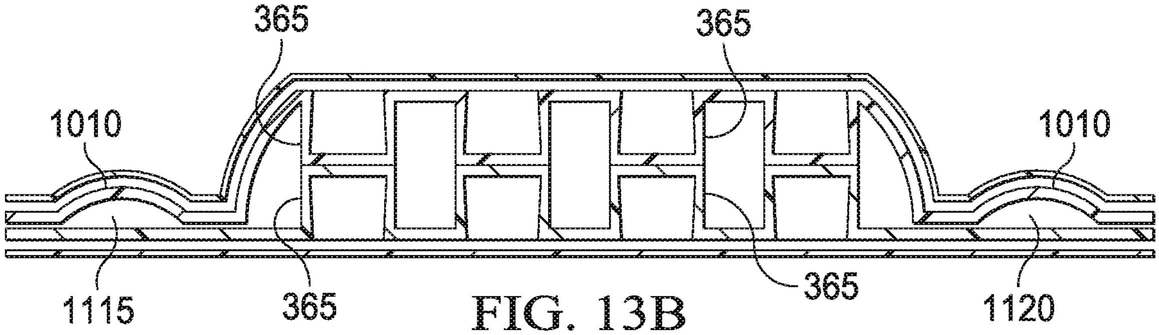
FIG. 13B is a schematic view taken along line 13B-13B of FIG. 13A.
Figure 13C:
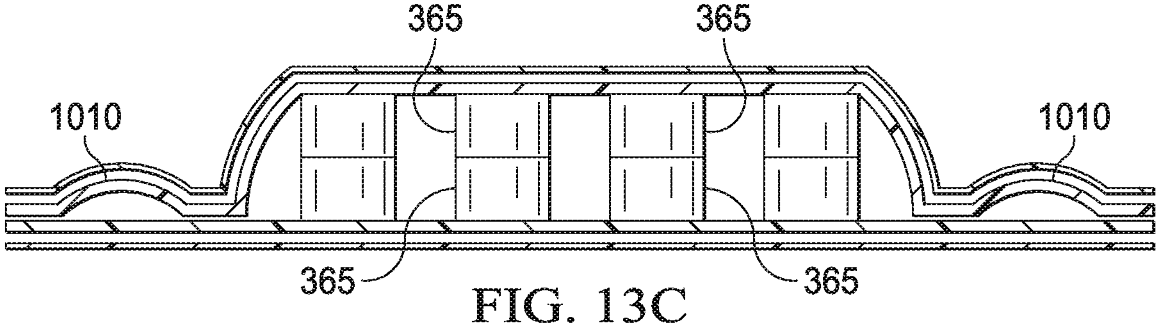
FIG. 13C is a schematic view taken along line 13C-13C of FIG. 13A.

FIG. 13A is a schematic view of another example configuration of fluid pathways in the bridge 160 of FIG. 10 as assembled, illustrating additional details that may be associated with some embodiments. FIG. 13B is a schematic view taken along line 13B-13B, and FIG. 13C is a schematic view taken along line 13C-13C. The example of FIG. 13A includes four rows of the supports 365, which are aligned both horizontally and vertically rather than being offset or staggered with each other. In some embodiments, the first fluid conductor 1115 and the second fluid conductor 1120 may be opened and supported by increasing the thickness of the spacer layer 1010.

Figure 14:
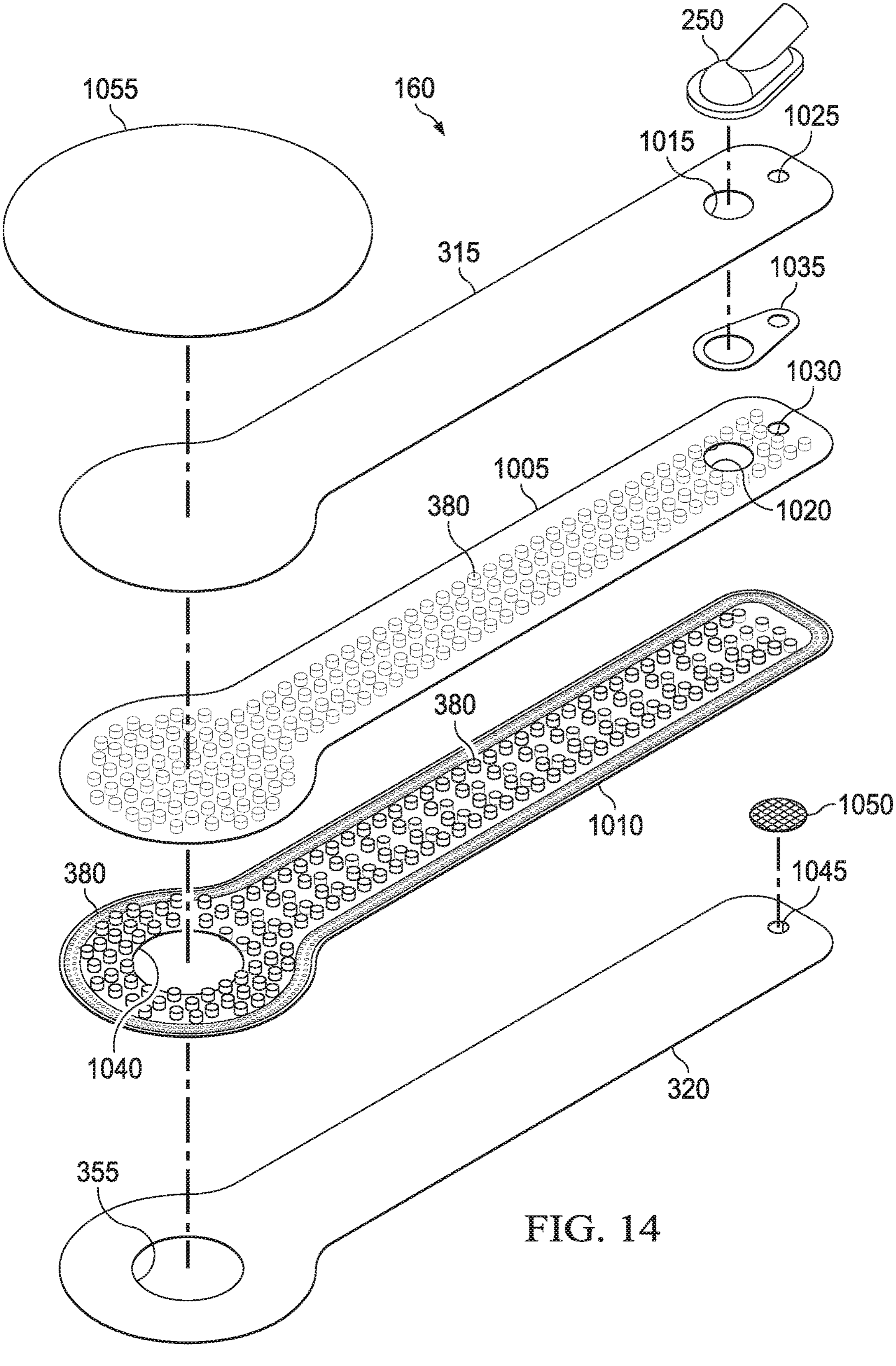
FIG. 14 is an assembly view of another example of a bridge.

FIG. 14 is an assembly view of another example of the bridge 160. In the example of FIG. 14, some of the standoffs 380 extend from the spacer layer 1010 away from the second layer 320 and some of the standoffs 380 may extend from the spacer layer 1010 toward the second layer 320. In some embodiments, the standoffs 380 that extend from the spacer layer 1010 toward the second layer 320 may be smaller in diameter than the standoffs 380 that extend from the spacer layer 1010 away from the second layer 320. In some embodiments, the standoffs 380 that extend from the spacer layer 1010 toward the second layer 320 may have a length less than a length of the standoffs 380 that extend from the spacer layer 1010 away from the second layer 320. As illustrated in FIG. 14, in some embodiments, the number of the standoffs 380 that extend from the spacer layer 1010 toward the second layer 320 may be less than the number of standoffs 380 that extend from the spacer layer 1010 away from the second layer 320. In some embodiments, a plurality of standoffs 380 that extend toward the second layer 320 may be located in the spacer layer 1010 at the end of the spacer layer 1010 proximate the aperture 1045.

Figure 15A:
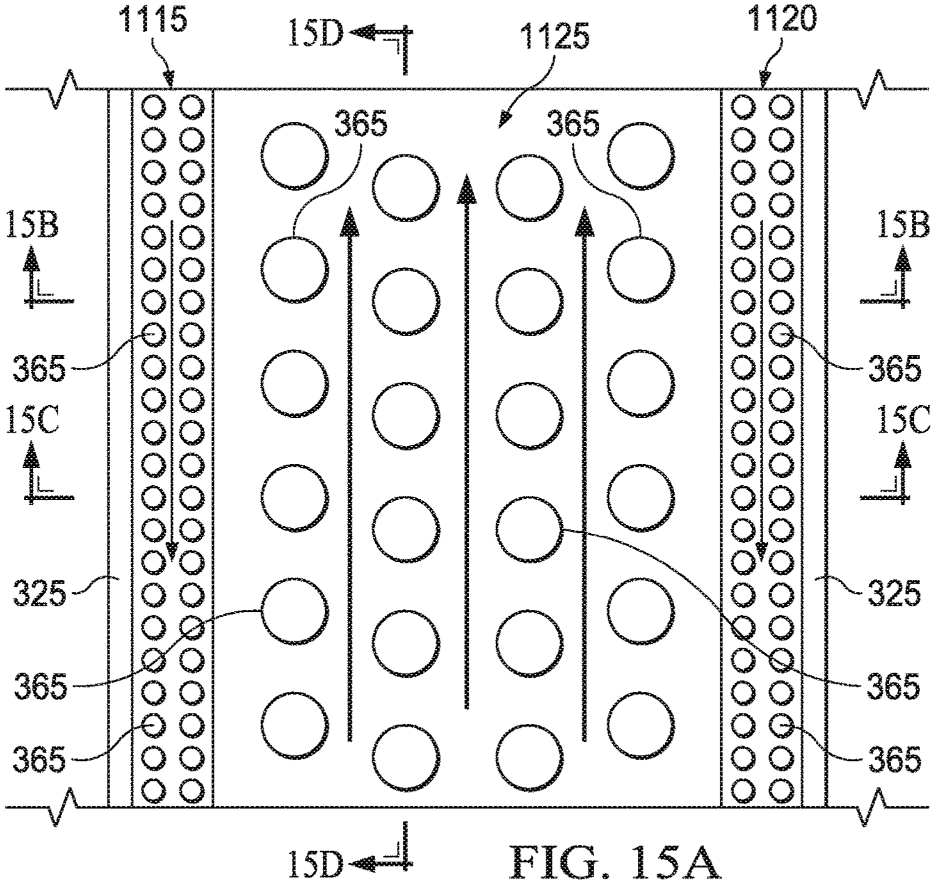
FIG. 15A is a schematic view of an example configuration of fluid pathways in the bridge of FIG. 14 as assembled, illustrating additional details that may be associated with some embodiments.
Figure 15B:
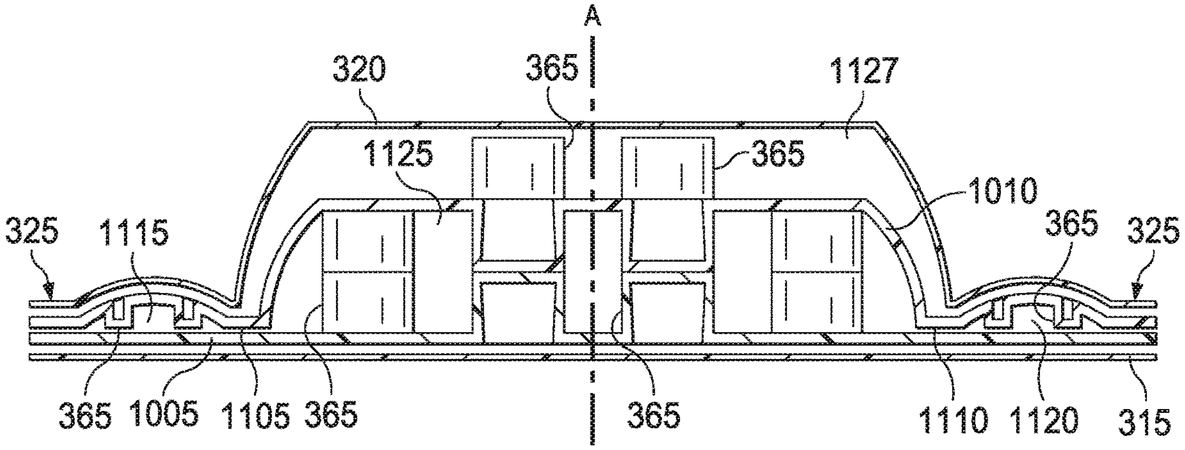
FIG. 15B is a schematic view taken along line 15B-15B of FIG. 15A.
Figure 15C:
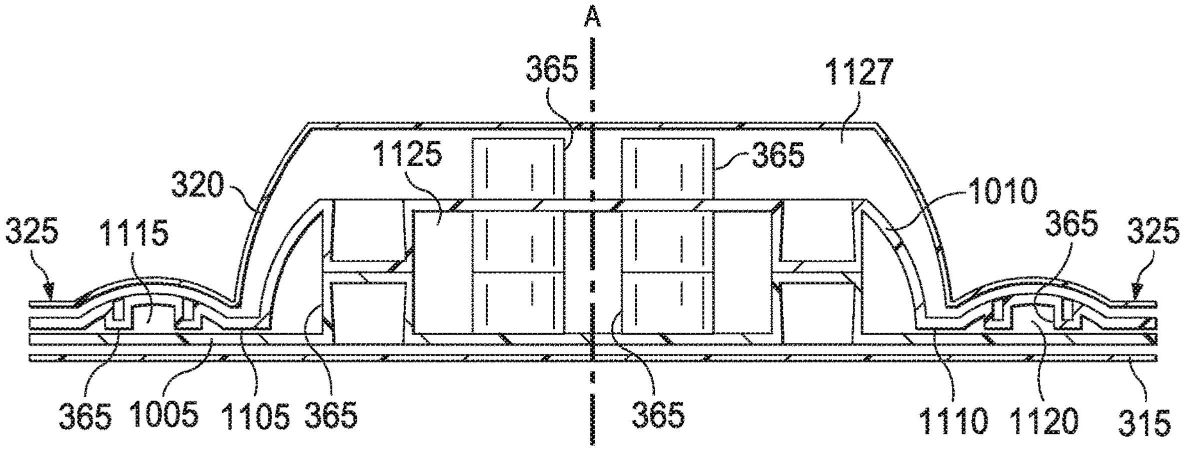
FIG. 15C is a schematic view taken along line 15C-15C of FIG. 15A.
Figure 15D:
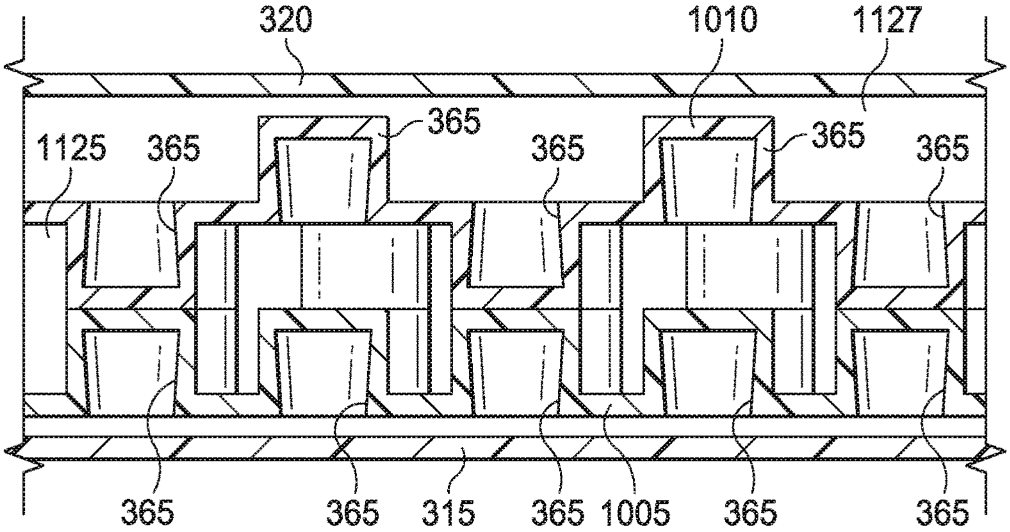
FIG. 15D is a schematic view taken along line 15D-15D of FIG. 15A.

FIG. 15A is a schematic view of an example configuration of fluid pathways in the bridge 160 of FIG. 14 as assembled. In the example of FIG. 15A, the bridge 160 has four rows of the supports 365, and the supports 365 forming outside rows are offset or staggered from the supports 365 forming the two inside rows. FIG. 15B is a schematic view taken along line 15B-15B, FIG. 15C is a schematic view taken along line 15C-15C, and FIG. 15D is a schematic view taken along line 15D-15D. The supports 365 may have a variety of shapes, and may be sized and arranged in different patterns within the third fluid conductor 1125. For example, as illustrated in the examples of FIG. 15B, FIG. 15C, and FIG. 15D, some of the supports 365 may extend from the spacer layer 1010 away from the second layer 320 and some of the supports 365 may extend from the spacer layer 1010 toward the second layer 320. In some embodiments, as illustrated in FIG. 15B and FIG. 15C, the supports 365 that extend from the spacer layer 1010 toward the second layer 320 may be symmetrically disposed proximate a longitudinal plane A of the bridge 160. In some embodiments, as illustrated in FIG. 15D, the supports 365 in spacer layer 1010 may alternate between extending toward the second layer 320 and away from the second layer 320. As illustrated in FIG. 15B, FIG. 15C, and FIG. 15D, the supports 365 that extend from the spacer layer 1010 toward the second layer 320 may be disposed within the fourth fluid conductor 1127. The supports 365 that extend from the spacer layer 1010 toward the second layer 320 may be configured to prevent or reduce collapse of the fourth fluid conductor 1127 upon the application of negative pressure.

Figure 16:
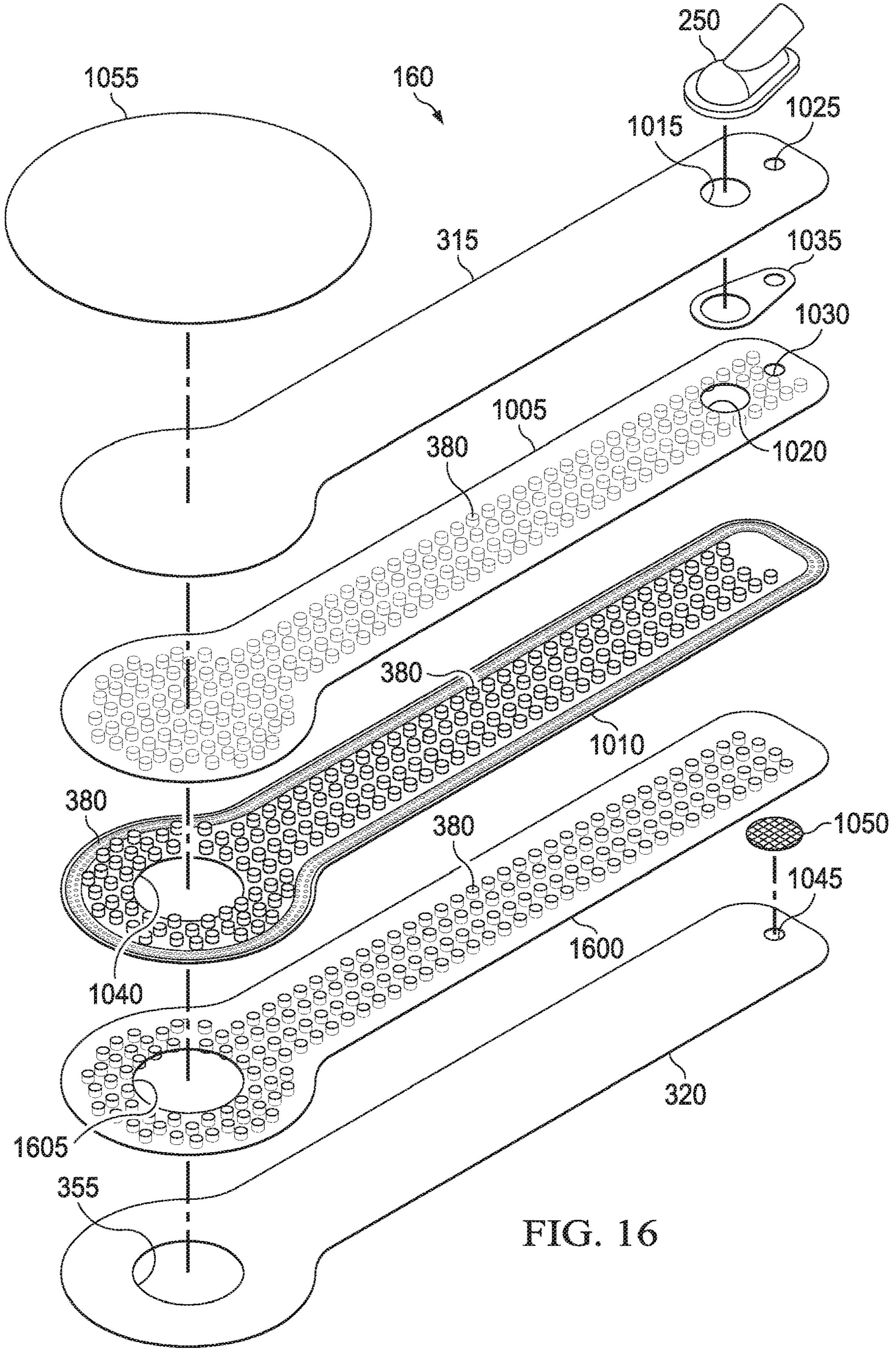
FIG. 16 is an assembly view of another example of a bridge.

FIG. 16 is an assembly view of another example of the bridge 160. In the example of FIG. 16, the bridge 160 may comprise a spacer layer 1600 disposed between the spacer layer 1010 and the second layer 320. Standoffs 380 may be formed in the spacer layer 1600. In the example of FIG. 16, the standoffs 380 in the spacer layer 1600 are configured to extend toward the second layer 320. The spacer layer 1600 may have an aperture 1605 concentric with the aperture 355 of the second layer 320 and the aperture 1040 of the spacer layer 1010.

Figure 17A:
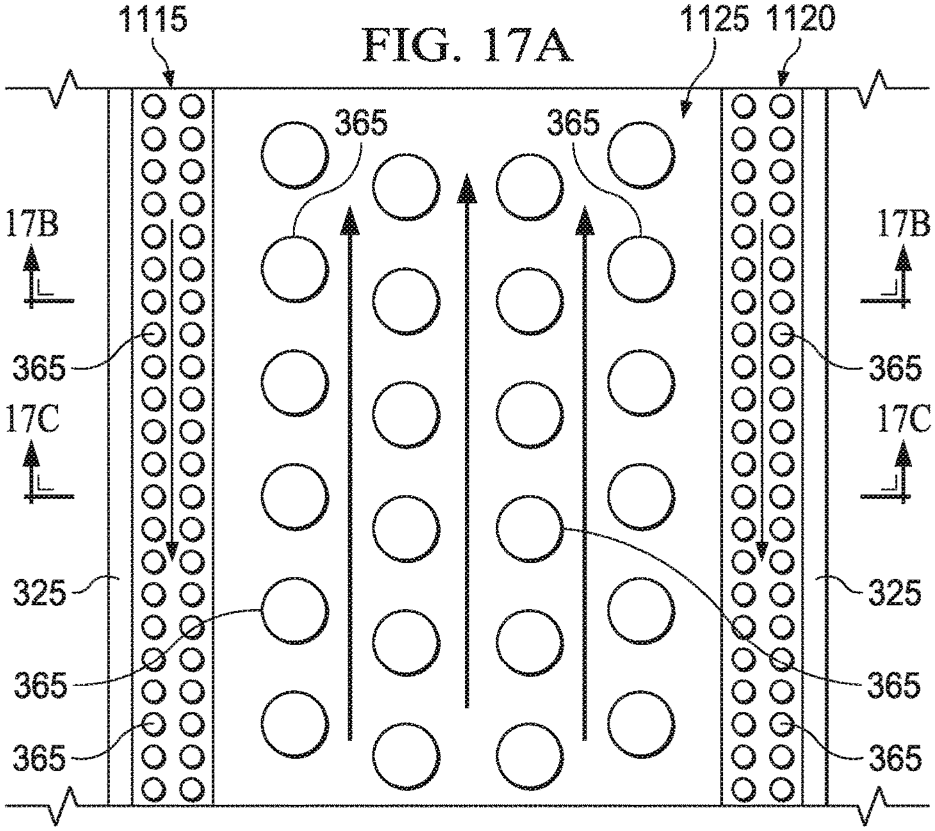
FIG. 17A is a schematic view of an example configuration of fluid pathways in the bridge of FIG. 16 as assembled, illustrating additional details that may be associated with some embodiments.
Figure 17B:
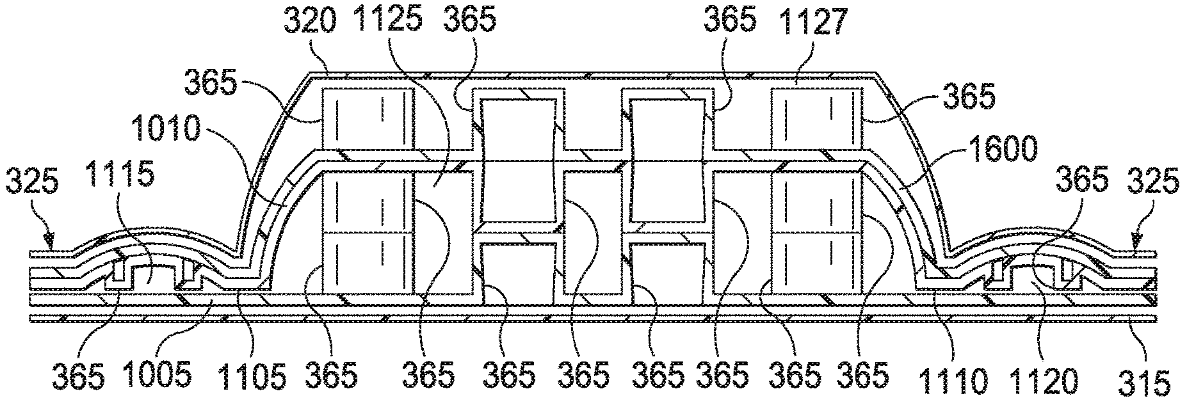
FIG. 17B is a schematic view taken along line 17B-17B of FIG. 17A.
Figure 17C:
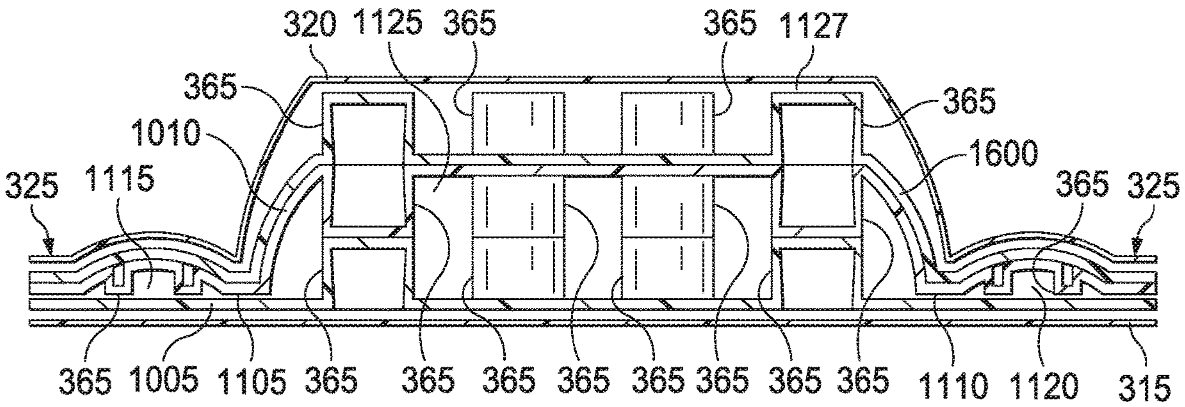
FIG. 17C is a schematic view taken along line 17C-17C of FIG. 17A.

FIG. 17A is a schematic view of an example configuration of fluid pathways in the bridge 160 of FIG. 16 as assembled. In the example of FIG. 17A, the bridge 160 has four rows of the supports 365, and the supports 365 forming outside rows are offset or staggered from the supports 365 forming the two inside rows. FIG. 17B is a schematic view taken along line 17B-17B, and FIG. 17C is a schematic view taken along line 17C-17C. The supports 365 may have a variety of shapes, and may be sized and arranged in different patterns within the third fluid conductor 1125. For example, as illustrated in the examples of FIG. 17B and FIG. 17C, some of the supports 365 may extend from the spacer layer 1600 away from the spacer layer 1010 and toward the second layer 320. In some embodiments, at least some of the supports 365 can extend from the spacer layer 1010 away from some of the supports 365 extending from the spacer layer 1600. Additionally, at least some of the supports 365 extending from the spacer layer 1010 may have an end that is open and at least some of the supports 365 extending from the spacer layer 1600 may have an end that is open, wherein at least some of the open ends of the supports 365 extending from the spacer layer 1010 abut at least some of the open ends of the supports 365 extending from the spacer layer 1600. In some embodiments, at least some of the supports 365 extending from the spacer layer 1010 and at least some of the supports 365 extending from the spacer layer 1600 cooperate to form a sealed space. As illustrated in FIG. 17B and FIG. 17C, the supports 365 that extend from the spacer layer 1600 may be disposed within the fourth fluid conductor 1127. The supports 365 that extend from the spacer layer 1600 may be configured to prevent or reduce collapse of the fourth fluid conductor 1127 upon the application of negative pressure.

Figure 18:
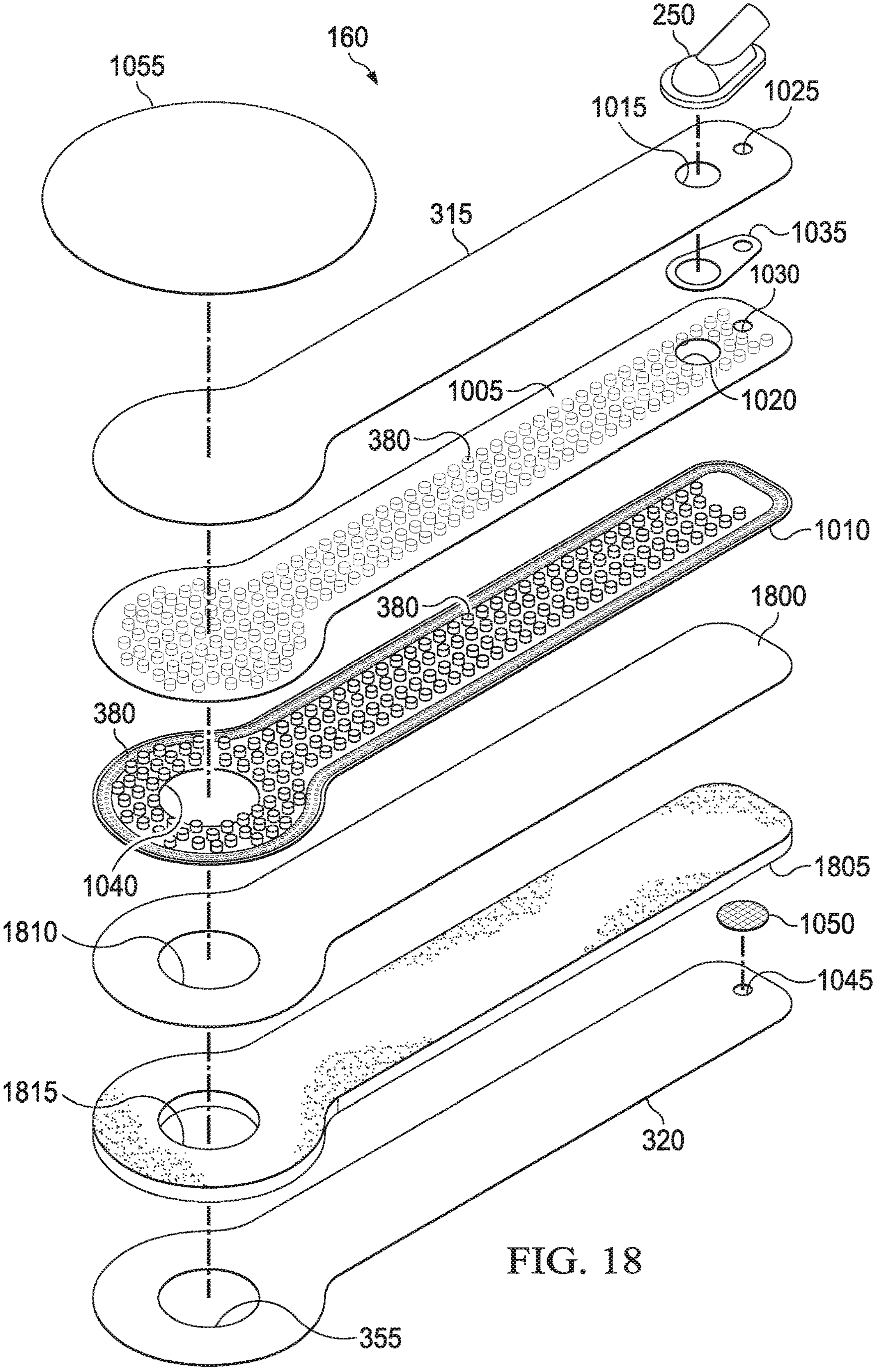
FIG. 18 is an assembly view of another example of a bridge.

FIG. 18 is an assembly view of another example of the bridge 160. In the example of FIG. 18, the bridge 160 may further include a third layer 1800 and a spacer layer 1805. The third layer 1800 may be disposed between the spacer layer 1010 and the second layer 320. The spacer layer 1805 may be disposed between the third layer 1800 and the second layer 320. The third layer 1800 may have an aperture 1810 concentric with the aperture 355 of the second layer 320 and the aperture 1040 of the spacer layer 1010. The spacer layer 1805 may have an aperture 1815 concentric with the aperture 355 of the second layer 320, the aperture 1810 of the third layer 1800, and the aperture 1040 of the spacer layer 1010.

The third layer 1800 may be formed from or include a film of liquid-impermeable material. In some examples, the third layer 1800 may be formed from the same material as the first layer 315. In some examples, the third layer 1800 may be formed from the same material as the cover 125. The spacer layer 1805 may be formed of a variety of materials and configurations that are open to pressure and fluid flow, particularly in the form of air. In some examples, the spacer layer 1805 may be hydrophobic to discourage ingress of exudate, and should resist blocking under compression. Additionally or alternatively, anti-clotting agents may be bound to the spacer layer 1805. Examples of materials suitable for some embodiments of the spacer layer 1805 may include reticulated foam (preferably having a thickness in a range of about 3 millimeters to about 5 millimeters), felted and compressed reticulated foam (preferably having a thickness in a range of about 2 millimeters to about 4 millimeters), combinations of foam and textiles (such as various textiles manufactured by Milliken & Company), or coated or treated foam (such as plasma treated). Additionally or alternatively, the spacer layer 1805 may comprise or consist essentially of a low-profile 3D polyester textile, such as textiles manufactured by Baltex.

Figure 19A:
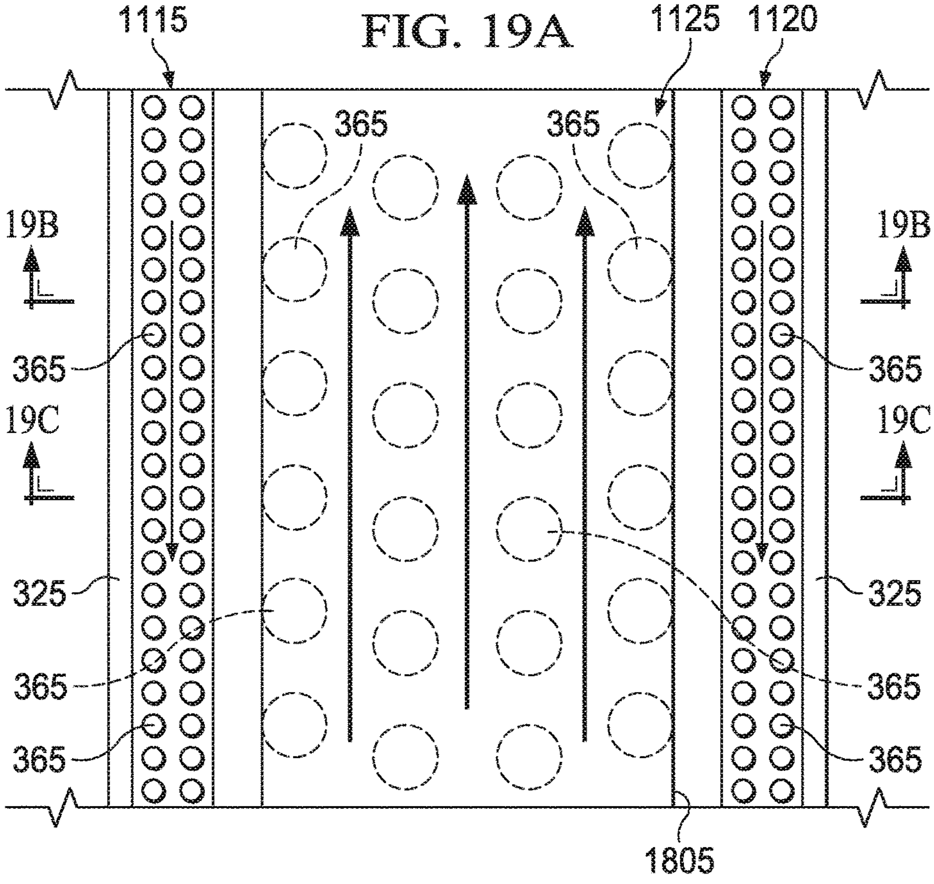
FIG. 19A is a schematic view of an example configuration of fluid pathways in the bridge of FIG. 18 as assembled, illustrating additional details that may be associated with some embodiments.
Figure 19B:
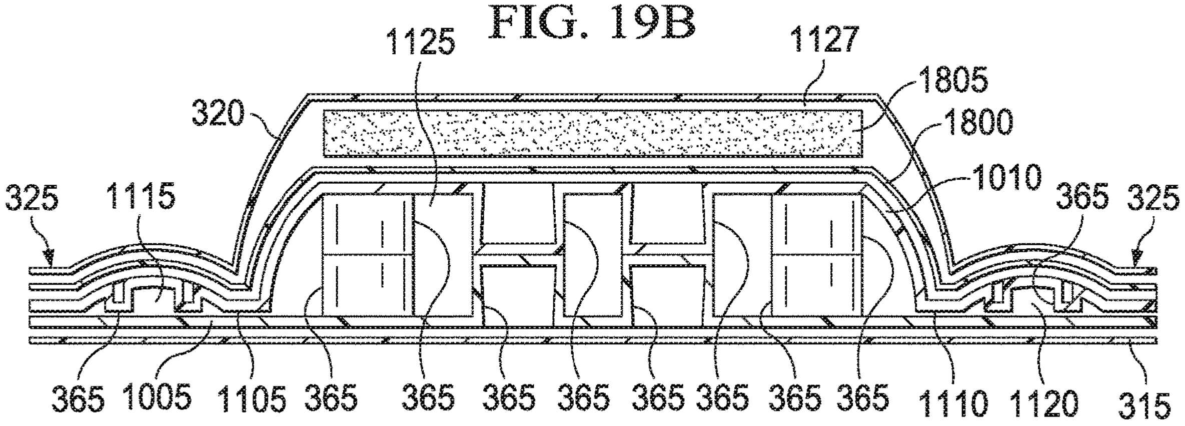
FIG. 19B is a schematic view taken along line 19B-19B of FIG. 19A.
Figure 19C:
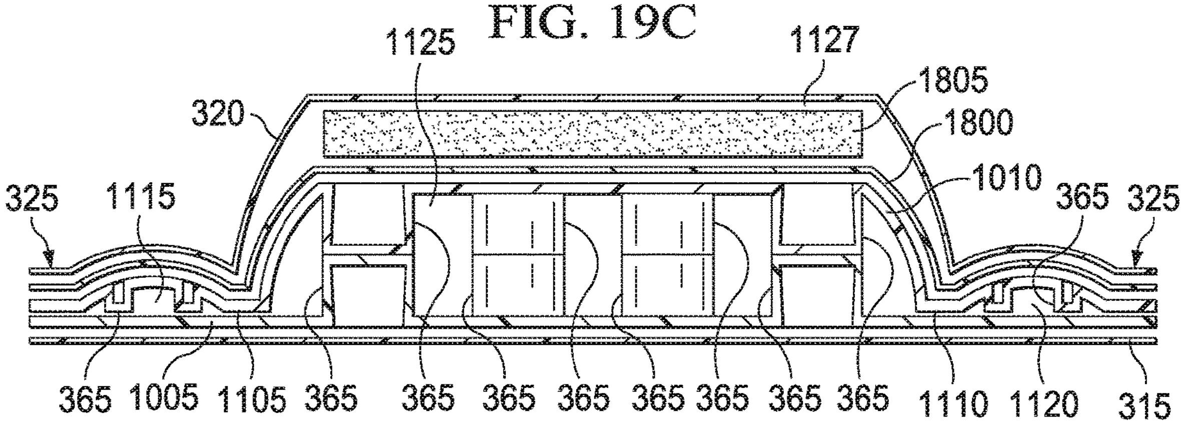
FIG. 19C is a schematic view taken along line 19C-19C of FIG. 19A.

FIG. 19A is a schematic view of an example configuration of fluid pathways in the bridge 160 of FIG. 18 as assembled. FIG. 19B is a schematic view taken along line 19B-19B, and FIG. 19C is a schematic view taken along line 19C-19C. As illustrated in the examples of FIG. 19B and FIG. 19C, the first wall 1105, the second wall 1110, the second layer 320, and the third layer 1800 may cooperate to form the fourth fluid conductor 1127. Thus, the fourth fluid conductor 1127 may be between the second layer 320 and the third layer 1800. The spacer layer 1805 may support the fourth fluid conductor 1127 and may be configured to prevent or reduce collapse of the fourth fluid conductor 1127 upon the application of negative pressure.

Figure 20:
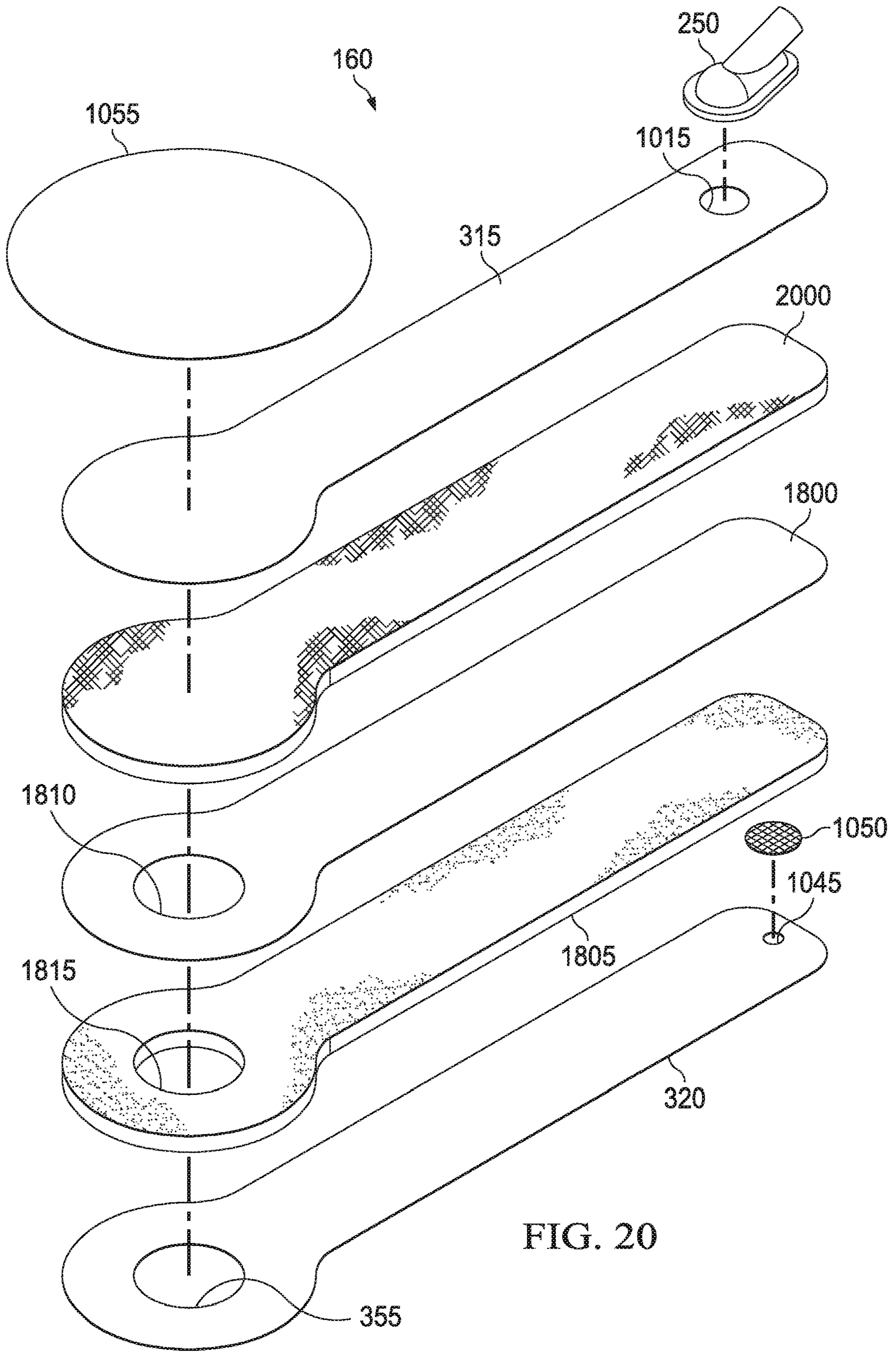
FIG. 20 is an assembly view of another example of a bridge.

FIG. 20 is an assembly view of another example of the bridge 160. In the example of FIG. 20, the bridge 160 may comprise a spacer layer 2000 disposed between the first layer 315 and the third layer 1800. The spacer layer 2000 may be formed of a variety of materials and configurations that are open to pressure and fluid flow, particularly in the form of air and exudate of varying viscosity. In some examples, the spacer layer 2000 may be hydrophobic to discourage collection and clotting of exudate, and should resist blocking under compression. Additionally or alternatively, anti-clotting agents may be bound to the spacer layer 2000. In some embodiments, the spacer layer 2000 may be less hydrophobic than the spacer layer 1805. Additionally or alternatively, the spacer layer 2000 may have a higher stiffness modulus than the spacer layer 1805. Examples of materials suitable for some embodiments of the spacer layer 2000 may include reticulated foam (preferably having a thickness in a range of about 3 millimeters to about 8 millimeters), combinations of foam and textiles (such as various textiles manufactured by Milliken & Company), or coated or treated foam (such as plasma treated). Additionally or alternatively, the spacer layer 2000 may comprise or consist essentially of a low-profile 3D polyester textile, such as textiles manufactured by Baltex.

Figure 21:
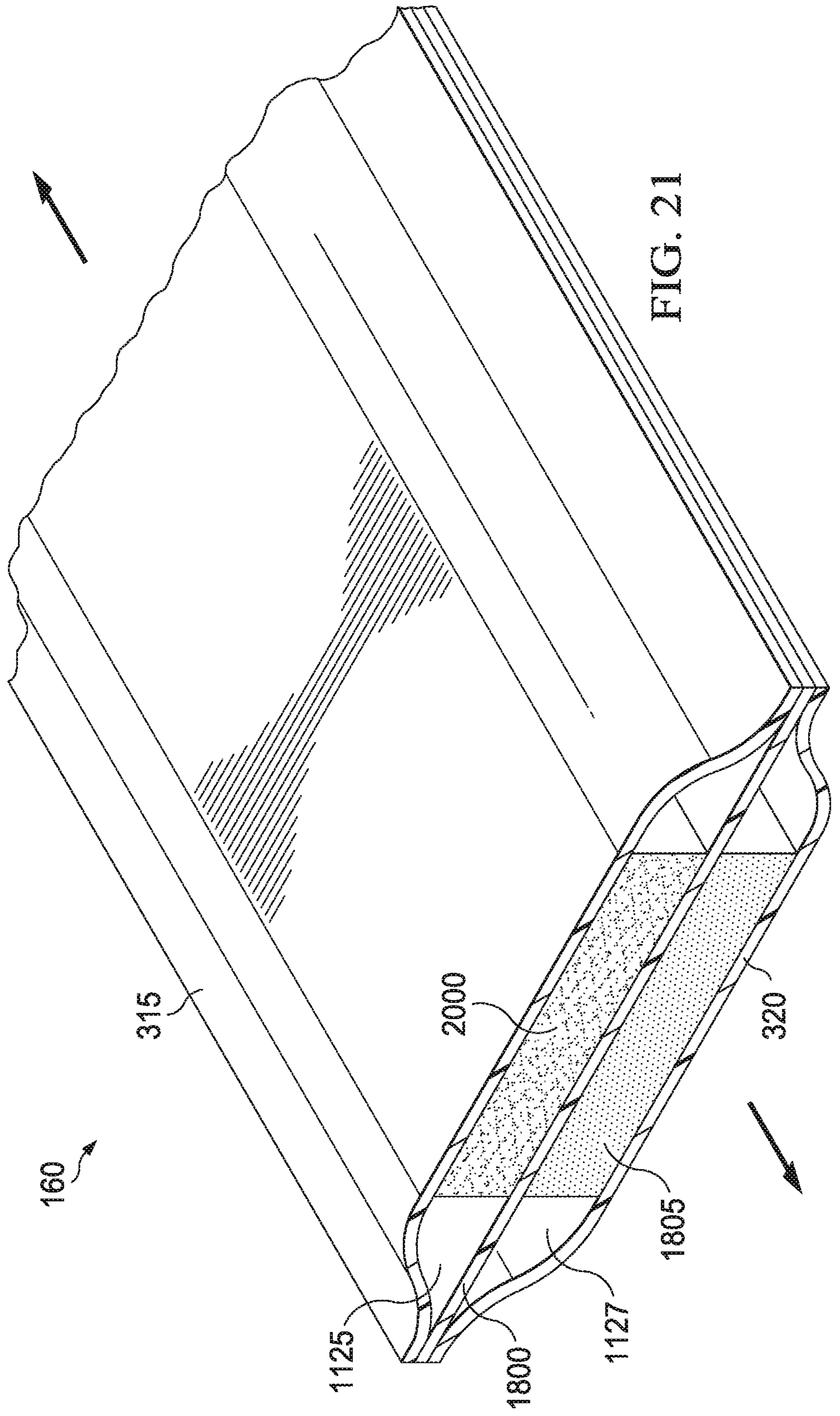
FIG. 21 is an assembled section view of the bridge of FIG. 20.

FIG. 21 is an assembled section view of the bridge 160 of FIG. 20. For example, the first layer 315, the second layer 320, and the third layer 1800 may be welded or bonded together to form two longitudinal chambers that run the length of the bridge 160. In the example of FIG. 21, edges of the first layer 315 and the second layer 320 are sealed to edges of the third layer 1800 to form the third fluid conductor 1125 and the fourth fluid conductor 1127 in a stacked relationship. The third layer 1800 is disposed between and fluidly separates the third fluid conductor 1125 and the fourth fluid conductor 1127. The spacer layer 2000 is configured to support the third fluid conductor 1125, separating a central portion of the first layer 315 and the third layer 1800. The spacer layer 2000 may be configured to prevent or reduce collapse of the third fluid conductor 1125 upon the application of negative pressure. The spacer layer 1805 is configured to support the fourth fluid conductor 1127, separating the second layer 320 and the third layer 1800. The spacer layer 1805 may be configured to prevent or reduce collapse of the fourth fluid conductor 1127 upon the application of negative pressure.

In other examples, a fourth layer (not shown) may be integrated to form a third chamber configured to deliver instillation solution or pressure sensing. The fourth layer may be comprised of a material similar to either of the first layer 315, the second layer 320, or the third layer 1800, for example. In some embodiments, the third chamber may have a volume that is less than the volume of the third fluid conductor 1125, and may be less than half the volume of the third fluid conductor 1125 in some examples.

Alternatively, in some embodiments of the bridge 160, the third fluid conductor 1125 and the fourth fluid conductor 1127 may be disposed side-by-side instead of in a stacked relationship. A side-by-side configuration may be assembled with only two film layers in some examples.

Figure 22:
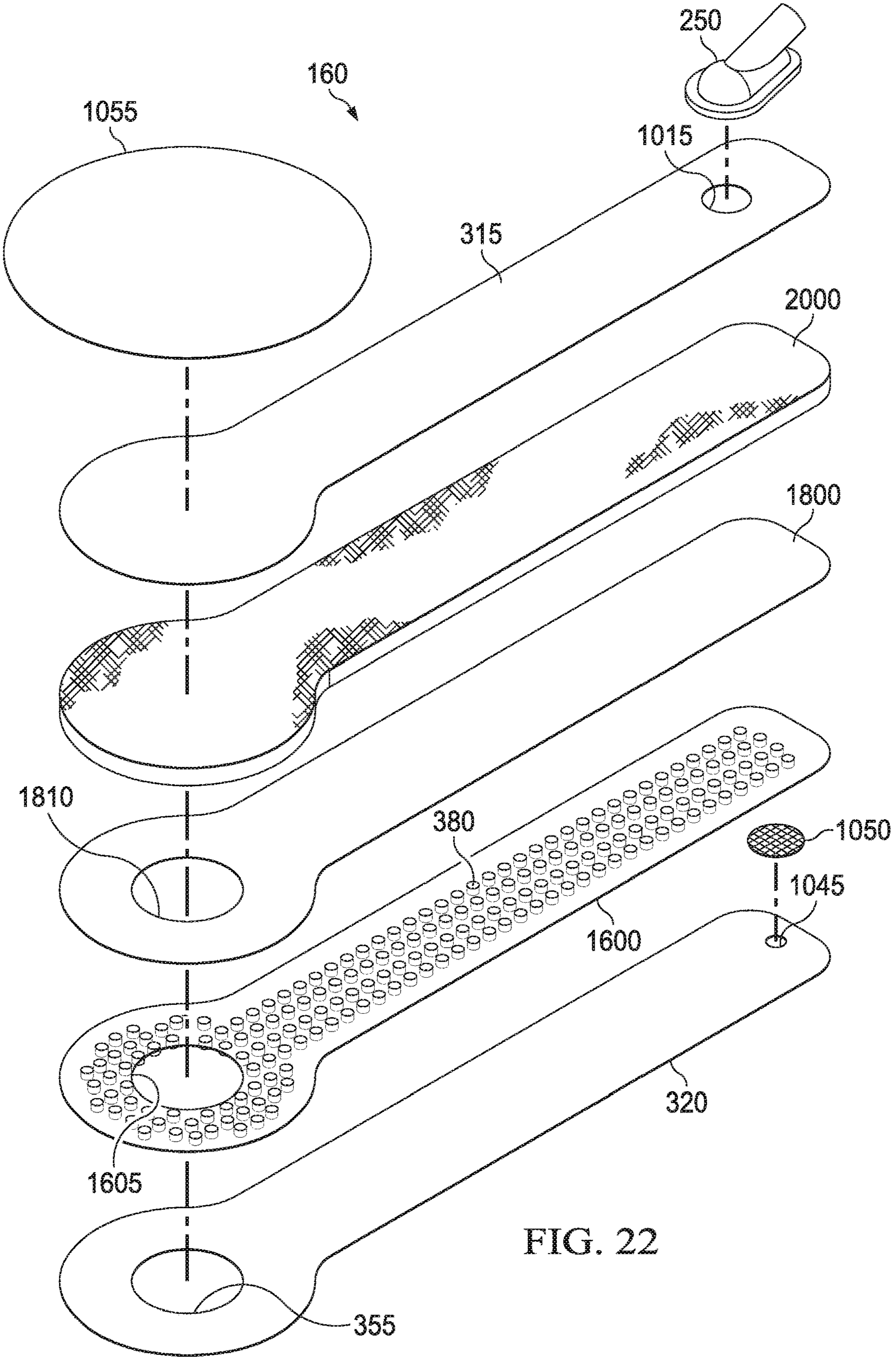
FIG. 22 is an assembly view of another example of a bridge.

FIG. 22 is an assembly view of another example of the bridge 160. In the example of FIG. 20, the bridge 160 may comprise the first layer 315, the spacer layer 2000, the third layer 1800, the spacer layer 1600, and the second layer 320 in a stacked relationship. For example, the spacer layer 2000 may be disposed between the first layer 315 and the third layer 1800, and the spacer layer 1600 may be disposed between the third layer 1800 and the second layer 320.

Figure 23:
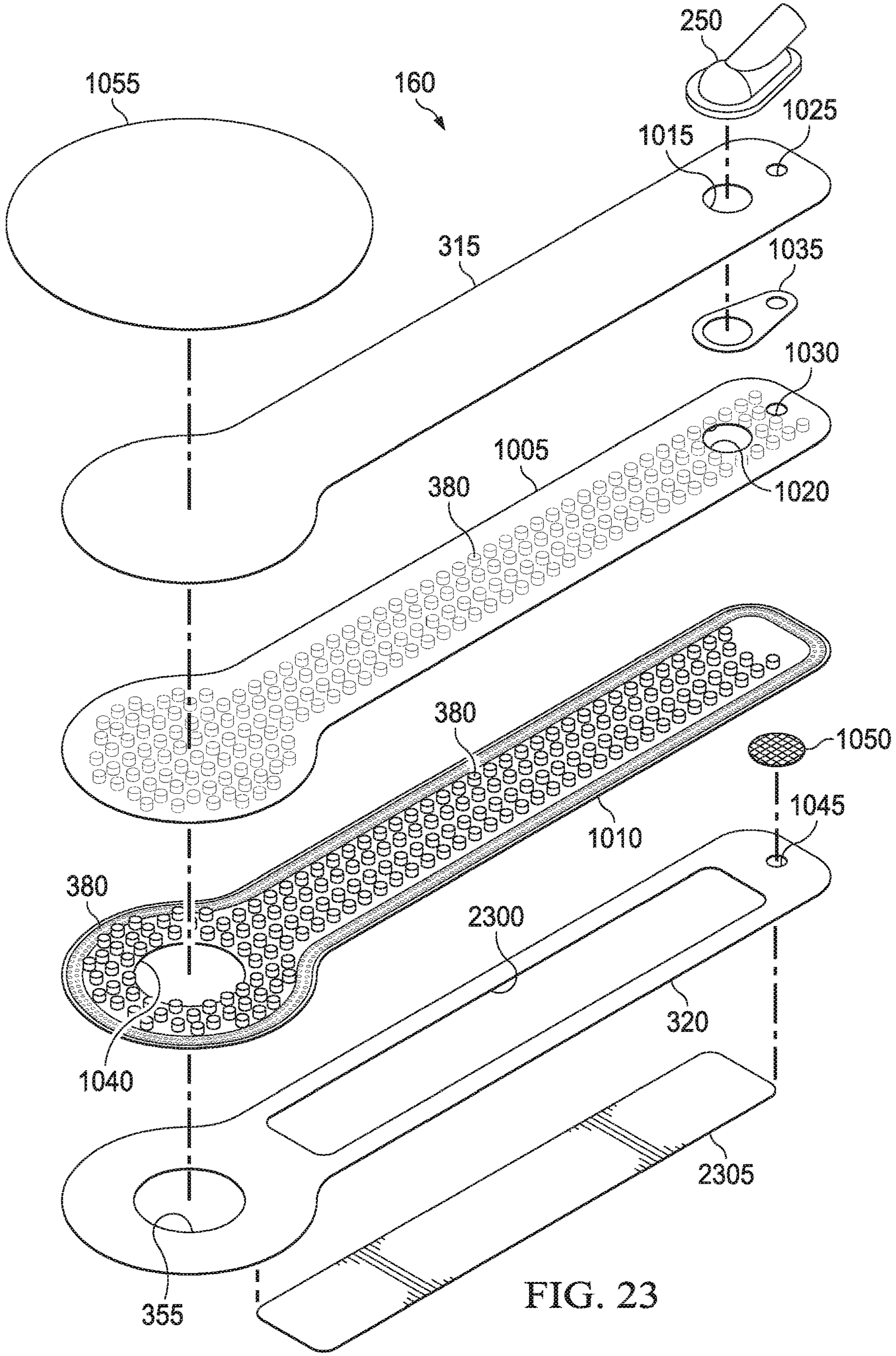
FIG. 23 is an assembly view of another example of a bridge.

FIG. 23 is an assembly view of another example of the bridge 160. In the example of FIG. 23, the second layer 320 may include a window 2300. A panel 2305 may be coupled to the second layer 320 to cover the window 2300. For example, the panel 2305 may be coupled to the second layer 320 by adhesives or welding. The panel 2305 may be a film having a high MVTR in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties. In some embodiments, the panel 2305 may comprise or consist essentially of a polymer film, such as Inspire 2301 and Inpsire 2304 polyurethane films, commercially available from Expopack Advanced Coatings, Wrexham, United Kingdom. In some embodiments, the panel 2005 may comprise INSPIRE 2301 having an MVTR (upright cup technique) of 2600-2700 $g/m^2/24$ hours and a thickness of about 30 microns. In some embodiments, the panel 2305 may comprise INSPIRE 2304 having an MVTR (upright cup technique) of 2600 $g/m^2/24$ hours and a thickness of about 30 microns. The panel 2305 may be oriented to permit moisture-vapor transmission through the panel 2305 toward the first layer 315. In embodiments where the panel 2305 is utilized, the second layer 320 need not comprise a material that has a high MVTR. Instead, the second layer 320 may comprise or consist essentially of a film having a higher thickness for durability. In some embodiments, the second layer 320 may comprise or consist essentially of a polyurethane film having a thickness of about 80 microns.

Figure 24:
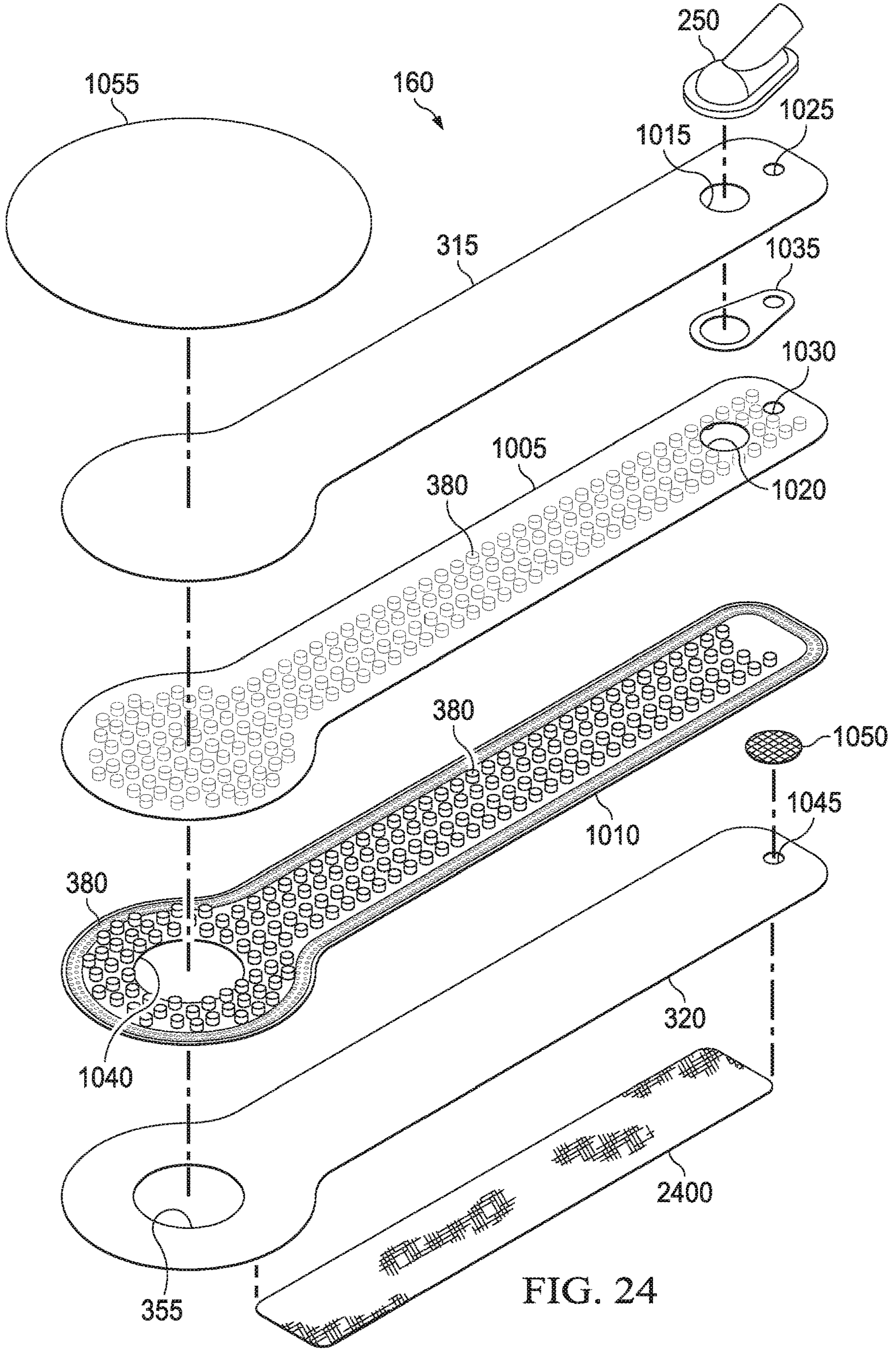
FIG. 24 is an assembly view of another example of a bridge.

FIG. 24 is an assembly view of another example of the bridge 160. In the example of FIG. 24, the bridge 160 may further include a moisture offloading layer 2400. In some embodiments, the moisture offloading layer 2400 may be coupled to the second layer 320 opposite to the first layer 315. In some embodiments, the second layer 320 may be coated with the moisture offloading layer 2400. The moisture offloading layer 2400 may be configured to contact the tissue site for wicking fluids from the periwound.

The moisture offloading layer 2400 may comprise or consist essentially of a non-woven material such as, for example, a polyester non-woven material such as, for example, Libeltex TDL4. In some embodiments, other non-woven structures may be used such as, for example, Libeltex TDL2, or laminations with fiber or foam structures. Further, other materials may be used, such as a polyurethane film having a high MVTR that may provide for evaporation of condensate. In other embodiments, the moisture offloading layer 2400 may comprise or consist essentially of materials that are hydrophilic in nature such as, for example, gels and foams that may be used to provide wicking and/or evaporation. For example, such materials may include one or more the following materials: hydrophilic polyurethane; cellulosics; hydrophilic polyamides; polyvinyl alcohol; polyvinyl pyrrolidone; hydrophilic acrylics; hydrophilic silicone elastomers; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; EVA film; co-polyester; silicones; a silicone drape; a 3M Tegaderm® drape; polyether block polyamide copolymer (PEBAX), for example, from Arkema, France; Expopack 2327; or other appropriate material. In some embodiments, the moisture offloading layer 2400 may comprise or consist essentially of Softesse 8801 commercially available from DuPont, Wilmington, Delaware.

Figure 25:
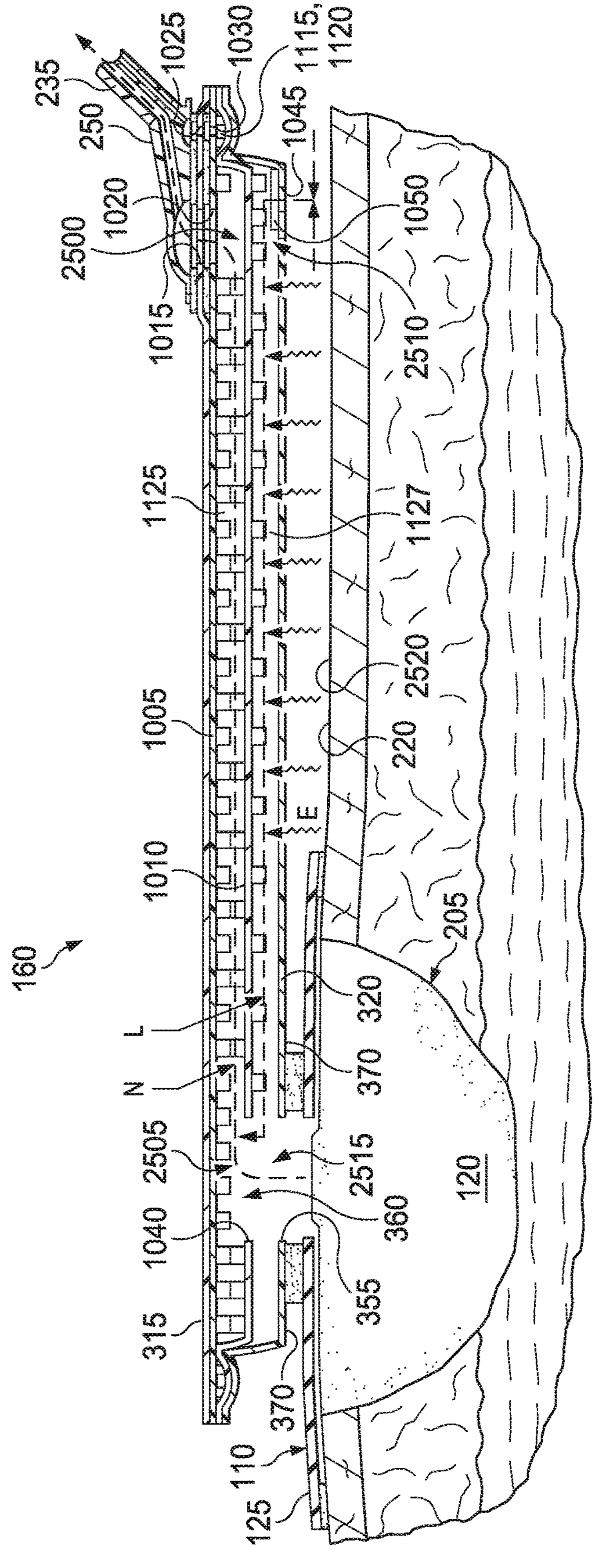
FIG. 25 is a schematic view of the bridge of FIG. 14 applied to a tissue site.

FIG. 25 is a schematic view of the bridge 160 of FIG. 14 applied to the tissue site 205. The third fluid conductor 1125 has a first end 2500 and a second end 2505. The fourth fluid conductor 1127 has a first end 2510 and a second end 2515. The passage 1015 and the passage 1025 may be disposed proximate the first end 2500 of the third fluid conductor 1125. The passage 1020 and the passage 1030 may be disposed proximate the first end 2500 of the third fluid conductor 1125. The aperture 1040 may be disposed proximate the second end 2505 of the third fluid conductor 1125. The aperture 1045 may be disposed proximate the first end 2510 of the fourth fluid conductor 1127, and the aperture 355 may be disposed proximate the second end 2515 of the fourth fluid conductor 1127. As further shown in FIG. 25, the aperture 1040 may fluidly couple the third fluid conductor 1125 to the fourth fluid conductor 1127. The dressing 110 may be fluidly coupled to the third fluid conductor 1125 and the fourth fluid conductor 1127 through the aperture 1040 and the aperture 355, respectively. The aperture 1045 may fluidly couple the fourth fluid conductor 1127 to the ambient environment. The hydrophobic filter 1050 may be disposed in the fourth fluid conductor 1127. Additionally, the adapter 250 may be fluidly coupled to the third fluid conductor 1127 through the aperture 1015 and the aperture 1020. The adapter 250 may also be fluidly coupled to the first fluid conductor 1115 and the second fluid conductor 1120 through the aperture 1025 and the aperture 1030. The adapter 250 may be fluidly coupled with the negative-pressure source 105 by conduit 235

As further shown in FIG. 25, the tissue interface 120 may be in fluid communication with the recessed space 360 through the aperture 355. The affixation surface 370 may be coupled to the cover 125 to seal and fluidly couple the recessed space 360 to the tissue interface 120. The bridge 160 may extend over and cover a portion of the epidermal layer 220 surrounding the tissue site 205, such as a periwound 2520. Moisture may evaporate from the periwound 2520 and pass through the second layer 320 into the fourth fluid conductor 1127 as shown by arrows E. Upon the application of negative pressure to the bridge 160, fluid can be drawn from the tissue site 205, into the recessed space 360, and through the third fluid conductor 1125, from the second end 2505 to the first end 2500 of the third fluid conductor 1125 (as shown by arrow N).

Additionally upon the application of negative pressure to the bridge 160, fluid is drawn from the ambient environment outside the bridge 160, through the aperture 1045, through the hydrophobic filter 1050, into the first end 2510 of the fourth fluid conductor 1127, through the fourth fluid conductor 1127, and toward the aperture 1040 and the aperture 355 at the second end 2515 of the fourth fluid conductor 1127 (as shown by arrow L). In addition to fluid drawn into the fourth fluid conductor 1127 through the aperture 1040, the evaporated moisture from the periwound 2520 that passed into the fourth fluid conductor 1127 through the second layer 320 is drawn through the fourth fluid conductor 1127 toward the aperture 1040, through the third fluid conductor 1125 and into the adapter 250. In some embodiments, moisture from the periwound 2520 that has not evaporated through second layer 320 may be drawn into the bridge 160 through the aperture 1045 and removed through the bridge 160. The aperture 1045 may provide a controlled flow through which moisture from the periwound 2520 can be removed from the periwound 2520. In some embodiments, the aperture 1045 may be dimensioned to provide a controlled flow in a range of about 25 cc/minute at −125 mmHg to about 250 cc/minute at −125 mmHg.

In embodiments with the hydrophobic filter 1050, the hydrophobic filter 1050 can prevent contents from the tissue site 205 from leaking out of the aperture 1045. Additionally, the hydrophobic filter 1050 can filter air going into the bridge 160 through the aperture 1045. The hydrophobic filter 1050 can prevent contamination inside and outside of the bridge 160.

The systems, apparatuses, and methods described herein may provide significant advantages. In some embodiments, the film construction of the first layer 315 and the second layer 315 may allow the bridge 160 to be conformable. In some embodiments, the bridge 160 may have a tensile stress at break of about 60 MPa, a tensile stress at 50% strain in a range of about 4 MPa to about 7 MPa, and a tensile strain at break (ultimate elongation) of about 540%. The bridge 160 may be sufficiently flexible to conform to the shape the tissue site 205. The bridge 160 may be sufficiently flexible or sized so that the bridge 160 may be folded to conform to a tissue site 205 to provide optimal negative pressure to the tissue site 205. When placed under a patient, the bridge 160 may also able to conform to the shape of the patient. The ability of the dressing 160 to conform may reduce discomfort to the patient and may reduce or eliminate occurrences of pressure sores if the patient sits or lies on the bridge 160.

The periwound 2520 ideally provides a barrier to the tissue site 205, which aids in protecting and confining the area of healing so that the tissue site 205 does not spread or increase in size. The periwound 2520 can become compromised when it is in excessive contact with moisture (e.g., wound fluid and/or sweat) for prolonged periods, which can cause the periwound 2520 to become soft or soggy and break down. This prolonged exposure of the periwound 2520 to moisture and the resulting deterioration of the epidermal layer 220 is defined as maceration. Maceration can negatively affect the healing progress of the tissue site 205 and can cause pain and/or discomfort to the patient. Some embodiments of the bridge 160 can reduce or eliminate maceration of the periwound 2520 that is proximate the bridge 160. For example, the evaporation of moisture from the periwound 2520 through the second layer 320 and into the fourth fluid conductor 1127 can reduce the moisture level at the periwound 2520, which can reduce maceration of the periwound 2520. Additionally, the ability to have fluid flow into the aperture 1045 and through the fourth fluid conductor 1127 of the bridge 160 aids in removing the moisture in the fourth fluid conductor 1127 that evaporated from the periwound 2520. The controlled flow provided by aperture 1045 may further remove moisture directly from the periwound 2520 and surrounding tissue and may bring dryer air to proximate the periwound 2520, which may further reduce the risk or occurrence of maceration. That is, the fluid drawn into the aperture 1045 from the ambient environment can evaporate moisture on the periwound 2520, surrounding tissue, or other surfaces between the bridge 160 and the patient. Reducing the risk or occurrence of maceration can improve patient comfort.

Additionally, some embodiments of the bridge 160 with the aperture 1045 may result in more consistent fluid removal from and negative-pressure delivery to the tissue site 205. For example, the aperture 1045, and the controlled flow provided by the aperture 1045, may aid in providing smoother negative pressure delivery to the tissue site over the course of negative-pressure therapy, as well as keeping the fluid and exudates removed from the tissue site 205 moving through the bridge 160 and therapy system 100 by providing a consistent open pathway. The bridge 160 with the aperture 1045 may reduce the risk of blockage of the third fluid conductor 1125.

While shown in a few illustrative embodiments, a person having ordinary skill in the art will recognize that the systems, apparatuses, and methods described herein are susceptible to various changes and modifications that fall within the scope of the appended claims. For example, in some embodiments, the bridge 160 may include a plurality of apertures along the length of the second layer 320, creating a plurality of inlets into the fourth fluid conductor 1127.

Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for conducting fluid, the apparatus comprising:
- a first layer comprising a first film;
- a second layer comprising a second film having a first aperture;
- a third layer comprising a third film having a second aperture and a third aperture, wherein:
  - the first layer, the second layer, and the third layer are sealed to form a first fluid pathway and a second fluid pathway in a stacked relationship,
  - the second layer is disposed between the first fluid pathway and the second fluid pathway;
  - the first aperture fluidly couples the first fluid pathway and the second fluid pathway;
  - the first aperture is fluidly coupled to the second aperture; and
  - the third aperture is fluidly coupled to the second fluid pathway and is configured to fluidly couple the second fluid pathway to the ambient environment;
- a first spacer layer configured to support the first fluid pathway; and
- a port fluidly coupled to the first fluid pathway.

2. The apparatus of claim 1, wherein:
- the first fluid pathway has a first end and a second end and the second fluid pathway has a first end and a second end; and
- the first aperture is proximate the second end of the first fluid pathway, the second aperture is proximate the second end of the second fluid pathway, and the third aperture is proximate the first end of the first fluid pathway.

3. The apparatus of claim 1, wherein in response to a negative pressure being applied to the first fluid pathway, fluid is configured to be drawn from the ambient environment through the third aperture, into the second fluid pathway, and toward the second aperture.

4. The apparatus of claim 1, further comprising a hydrophobic filter disposed over the third aperture.

5. The apparatus of claim 1, further comprising a second spacer layer configured to support the second fluid pathway.

6. The apparatus of claim 5, wherein the first spacer layer and the second spacer layer are hydrophobic.

7. The apparatus of claim 1, wherein the first spacer layer comprises open-cell foam or a textile.

8. The apparatus of claim 5, wherein the second spacer layer comprises open-cell foam or a textile.

9. The apparatus of claim 1, wherein the third film has a high moisture-vapor transmission rate and is configured to permit vapor pass through the third layer into the second fluid pathway.

10. The apparatus of claim 1, further comprising a moisture offloading layer coupled to the third layer opposite the first layer, the moisture offloading layer configured to contact a tissue site for wicking fluids from a periwound.

11. The apparatus of claim 1, wherein the port is configured to fluidly couple the first fluid pathway to a source of negative pressure.

12. The apparatus of claim 1, further comprising a dressing fluidly coupled to the first fluid pathway through the first aperture.

* * * * *